US009416401B2

(12) United States Patent
Söderlund et al.

(10) Patent No.: US 9,416,401 B2
(45) Date of Patent: Aug. 16, 2016

(54) METHOD FOR DETERMINING AMOUNTS OF POLYNUCLEOTIDE SEQUENCES PRESENT IN CELL OR TISSUE SAMPLES

(75) Inventors: Hans Söderlund, Espoo (FI); Kari Kataja, Espoo (FI); Marja Paloheimo, Vantaa (FI); Marja Ilmen, Helsinki (FI); Kristiina Takkinen, Espoo (FI)

(73) Assignee: VALTION TEKNILLINEN TUTKIMUSKESKUS, Espoo (FI)

( * ) Notice: Subject to any disclaimer, the term of this patent is extended or adjusted under 35 U.S.C. 154(b) by 1827 days.

(21) Appl. No.: 10/451,640

(22) PCT Filed: Jan. 10, 2002

(86) PCT No.: PCT/FI02/00023
§ 371 (c)(1),
(2), (4) Date: Jul. 10, 2003

(87) PCT Pub. No.: WO02/055734
PCT Pub. Date: Jul. 18, 2002

(65) Prior Publication Data
US 2004/0053300 A1    Mar. 18, 2004

(30) Foreign Application Priority Data
Jan. 10, 2001 (FI) .................................... 20010041

(51) Int. Cl.
*C12Q 1/68* (2006.01)
*C12M 1/34* (2006.01)
*G01N 33/567* (2006.01)
*G01N 33/00* (2006.01)
*C07K 1/00* (2006.01)
*C07K 16/00* (2006.01)
*C07H 21/04* (2006.01)

(52) U.S. Cl.
CPC ........ *C12Q 1/6816* (2013.01); *C12Q 2600/158* (2013.01)

(58) Field of Classification Search
USPC .......... 435/6, 91.1, 91.2, 183, 287.2; 436/94; 536/23.1, 24.31, 24.33
See application file for complete search history.

(56) References Cited

U.S. PATENT DOCUMENTS

| | | | | |
|---|---|---|---|---|
| 4,898,951 | A | * | 2/1990 | Symons ...................... 548/304.1 |
| 4,968,602 | A |   | 11/1990 | Dattagupta |
| 5,082,830 | A | * | 1/1992 | Brakel et al. ........................ 435/6 |
| 5,200,313 | A | * | 4/1993 | Carrico ............................... 435/6 |
| 5,340,714 | A | * | 8/1994 | Katsilometes ..................... 435/6 |
| 5,512,478 | A | * | 4/1996 | Orser et al. ................. 435/252.33 |
| 5,514,256 | A | * | 5/1996 | Douthart et al. ............... 204/464 |
| 5,547,835 | A | * | 8/1996 | Koster ................................. 435/6 |
| 5,633,134 | A |   | 5/1997 | Shuber |
| 5,667,976 | A | * | 9/1997 | Van Ness et al. .................. 435/6 |
| 5,686,242 | A | * | 11/1997 | Bruice et al. ....................... 506/1 |
| 5,714,386 | A | * | 2/1998 | Roederer ....................... 436/546 |
| 5,807,682 | A | * | 9/1998 | Grossman et al. ................. 435/6 |
| 5,981,171 | A |   | 11/1999 | Kuhns |
| 6,043,031 | A |   | 3/2000 | Köster et al. |
| 6,136,531 | A |   | 10/2000 | Leying et al. |
| 6,268,144 | B1 |   | 7/2001 | Koster |
| 6,395,486 | B1 |   | 5/2002 | Grossman |
| 6,480,791 | B1 |   | 11/2002 | Strathmann |
| 2002/0119455 | A1 | * | 8/2002 | Chan .................................. 435/6 |
| 2006/0286570 | A1 | * | 12/2006 | Rowlen et al. ..................... 435/6 |
| 2007/0009954 | A1 | * | 1/2007 | Wang et al. ........................ 435/6 |
| 2007/0031829 | A1 | * | 2/2007 | Yasuno et al. ..................... 435/6 |
| 2007/0042400 | A1 | * | 2/2007 | Choi et al. ......................... 435/6 |
| 2007/0042419 | A1 | * | 2/2007 | Barany et al. ..................... 435/6 |

FOREIGN PATENT DOCUMENTS

| | | |
|---|---|---|
| JP | 9-98799 | 4/1997 |
| JP | 2000-503845 | 4/2000 |
| WO | 99/37663 | 7/1999 |
| WO | WO 02/55734 | 1/2002 |

OTHER PUBLICATIONS

Stratagene Cloning Systems, 1993, pp. 120, 128, 143-145.*
Tenhunen et al., "A Solution Hybridization Method for Quantificaiton of mRNAs: Determining the Amount and Stability of Oncogene mRNA," Genetic Analysis Techniques and Applications, 7(8): 228-233, 1990.*
Zhang e tal., "Reconstruction of DNA sequencing by hybridization," Bioinformatics, vol. 19, No. 1, 2003, pp. 14-21.*
Tenhunen et al., "A Solution Hybridization Method for Quantification of mRNAs: Determining the Amount and Stability of Oncogene mRNA," GATA, vol. 7, No. 8, 1990, pp. 228-233.*
Tenhunen et al., "A Solution Hybridization Methof of Quantificaiton of mRNAs: Determining the Amount and Stability of Oncogene mRNA," GATA, 1990, 7(8):228-233.*
Zhang et al., Bioinformatics, vol. 19, No. 1, 2003, pp. 14-21.*
P. Eric Mayrand et al.: "Automation of Specific Human Gene Detection," Clin. Chem., vol. 36, No. 12, 1990, pp. 2063-2071, see p. 2067, left column, lines 15-51.

(Continued)

*Primary Examiner* — Bradley L Sisson
(74) *Attorney, Agent, or Firm* — Arent Fox LLP

(57) ABSTRACT

The invention is related to a method and test kits for quantitative determination of polynucleotide amounts present in a sample. The test kit comprises organized pools with polynucleotide probes having distinct sizes and optionally provided with tracer tags or primer tags. The probes are allowed to hybridize with affinity tagged analyte polynucleotides from the sample. The result is hybrids, which can be recovered on a separation aiding tool provided with the pair of the affinity tag. After the quantitative release of the probes, the probes are either directly recorded, or if primer tagged, they are amplified and optionally provided with a tracer tag before recording. The invention provides a sensitive and quantitative determination of the amount polynucleotides present in a cell or tissue sample and allows a quantitative assessment of variations in the amounts of polynucleotides as a response to inherent changes or due to external stimuli.

21 Claims, 12 Drawing Sheets

(56) References Cited

OTHER PUBLICATIONS

L. W. Chen-Liu et al.: "Selection of Hybrids by Affinity Capture (SHAC): A method for the Generation of cDNAs Enriched in Sequences from a Specific Chromosome Region," Genomics, vol. 30, 1995, pp. 388-392.

Syvanen AC et al.: "Quantification of polymerase chain reaction products by affinity-based hybrid collection, National Library of Medicine (NML), file Medline, Medline accession No. 2849762;" & Nucleic Acirds Res Dec. 9, 1988;16 (23): 11327-38.

Tenhunen J. et al.: "A solution hybridization method for quantification of mRNA determining the amount and stability of oncogene mRNA;" National Library of Medicine (NML), file Medline, Medline accession No. 2091699; & Genet Anal Tech Appl Dec. 1990; 7(8): 228-33.

Jukka Tenhunen et al.: "A solution Hybridization Method for Quantification of mRNAs: Determining the Amount and Stability of Oncogene mRNA," Genetic Analysis Techniques and Applications, vol. 7, No. 8 1990, pp. 229-233.

Olejnik, J. et al.: Photocleavable peptide-DNA conjugates synthesis and applications to DNA analysis using MALDI-MS, Nucleic Acids Research, vol. 27, 1999, s. 4626-4631.

Isola, N. R. et al.: MALDI-TOF Mass Spectrometric Method for Detection of Hybridized DNA Oligomers, Analytical Chemistry, vol. 73, No. 9, 2001, s. 2126-2131.

Amann et al., *Applied and Environ Microbiol*, 56:1919-1925 (1990).

\* cited by examiner

METHOD FOR DETERMINING AMOUNTS OF POLYNUCLEOTIDE SEQUENCES PRESENT IN CELL OR TISSUE SAMPLES

CROSS-REFERENCE TO RELATED APPLICATION

This application is a National Stage entry of International Application No. PCT/FI02/00023, filed Jan. 10, 2002.

THE TECHNICAL FIELD OF THE INVENTION

The present invention is related to a method for quantitative determination of the amounts of polynucleotides or variations in their amounts in a cell or tissue sample using organized pools of soluble polynucleotide probes with distinct sizes. The quantitative method allows comparative assessment of variations, e.g. in transcription profiles or expression patterns. The invention further relates to a test kit comprising means and reagents for carrying out the method of the present invention. Also disclosed is the use of said method and test kit for various diagnostic and biotechnical purposes.

THE BACKGROUND OF THE INVENTION

As a response to the rapid increase in available genetic information and its impact on molecular biology, health care, treatment modalities, pharmaceutical research, epidemiological studies, etc., the scientific interest is today focusing on the cellular effects of the genetical key elements as well as their biological role and functions. As the accumulation of new information related to the basic key elements in genetics is slowing down, the desire to study their effects and/or biological role is steadily increasing.

Bioinformatics, handling information related to life processes and accumulating in genomics, proteomics, transcriptomics, etc., in a mathematically exact manner has created a demand for new accurate tools allowing rapid and quantitative assessment of the effects and importance of the accumulated knowledge. Combinatorial chemistry allows rapid synthesis of an enormous amount of novel and already existing compounds. It is desirable to rapidly assess the effects and potential importance of said novel or already existing compounds or other external stimuli on the gene expression in living organisms, including human beings and experimental animals. In other words, the information accumulating in genomics, proteomics, transcriptomics, etc., as well as combinatorial chemistry combined with bioinformatics has created a demand for new tools allowing rapid, accurate and preferably quantitative assessment of the effects and biological role of said compounds. In fact, a significant market has grown up around the technology allowing transcriptional profiling. Transcriptional profiles are not only used by scientists in many areas of basic research in life sciences, but also in industrial research and development. The effects of known and novel drugs on the gene expression of human beings and experimental animals is today an essential knowledge in the pharmaceutical and diagnostic industry, but beneficiaries will also be several other sectors of the biotechnology industry.

A powerful tool in transcriptional profiling is the oligomer-chip technology, disclosed for example in the following U.S. Pat. No. 6,040,138, U.S. Pat. No. 5,556,752; U.S. Pat. No. 5,770,722, U.S. Pat. No. 5,807,522 or patent application WO 200003037. The U.S. Pat. No. 6,040,138 discloses the simultaneous monitoring of multiple gene expression by hybridizing target nucleic acids to an array of immobilized oligonucleotide probes. The U.S. Pat. No. 5,556,752 and U.S. Pat. No. 5,770,722 describe nucleic acid sequencing and methods of analysing by the aid of nucleic acid library arrays on solid supports as well as by applying hybridisation and nuclease or ligase reactions. In patent application WO 200003037 the screening of target polynucleotides on an array to determine their genetic function is disclosed. U.S. Pat. No. 5,807,522 discloses micro-arrays of certain analyte-assay regions containing analyte-specific reagents, which are useful for many genetic applications applying large-scale hybridisation techniques.

The common characteristic of the microarray techniques described above is that the probes, i.e. the polynucleotide sequences used as reagents are immobilized or coupled to a solid carrier. The immobilization of the probes acts as a steric hindrance and prevents the hybridization to take place in a stochiometric fashion resulting in low yield. Thus, the methods mentioned above are only semiquantitative and require double labeling and comparative checking.

Due to insufficient distinguishability caused, e.g. by blurred probe spots, it is often impossible to compare the spots with sufficient accuracy. Although this is not an obstacle for applying the micro-array techniques, it remains a problem, when quantitative results are needed and it explains why a large degree of redundancy is required in the actual tests. In the patent application WO 98/51789 the preparation of sub-divided cDNA libraries from mRNA by reverse transcription and amplification is described. The libraries are used for screening new genes, interacting proteins, potential drugs and/or for diagnosing. This system depends on PCR-technology and a set of different primers. Even if said system allows detection of down-regulated sequences present in low amounts, it increases quantification problems. Accordingly, powerful tools for studying the biological role of genetical key elements exist, but the problem of obtaining quantitative results still remains. Furthermore, the previous techniques are not applicable for monitoring the effects of uncharacterized genomes.

Thus, the main objective of the present invention is to provide a method and test kits not only for quantification of expression patterns or transcriptional profiles enabling comparative assessments of variations therein, but also to provide a very sensitive test, which allows the quantitative determination of very small amounts of analyte polynucleotides, which otherwise would be under the detection limit. The objective is to provide a truly quantitative method and test kit, which as an answer gives the amount of polynucleotide copies in the sample, e.g. allows the number of mRNA copies present in the sample to be assessed and which further can be modified to increase its sensitivity significantly.

An advantage of the method and test kit of the present invention is that it allows assessment of transcriptional profiles or expression patterns not only for characterized but also for uncharacterized genomes.

A further advantage of the present invention is that the quality of the analyte, i.e. the polynucleotide preparation, to be analyzed, is not critical. RNA, which generally, is known to require special treatment due to its instability, can be used directly for the quantitative assessment.

The manufacturing of test kits, which need not include immobilization steps and certain commercially available reagents allows easy adaptation of tailor-made tests, directing the attention to certain subsets of genes in a given organism.

The method is very adaptable. It can be used in fully automatic or semiautomatic assemblies. The procedure can be interrupted at several stages. The samples and reaction products can be preserved until sufficient data has been collected or it is more convenient to continue the process, e.g. recording the results.

A SUMMARY OF THE INVENTION

As a summary, the present invention allows quantification of changes and variations of the amounts of polynucleotides in nucleotide containing samples, which have been taken at different points of time, from different sites or from different target organisms. This is useful especially when studying life processes and the impact of physical and chemical stimuli applied on the same cells or tissues. The invention allows simultaneous comparative assessment of several biological phenomenons.

The method and test kit of the present invention is not only quantitative, it can also be made very sensitive and allow quantitative detection of down-regulated polynucleotide sequences. The characteristics of the method and test kit of the present invention are as defined in the claims.

A SHORT DESCRIPTION OF THE DRAWINGS

Figure 1:
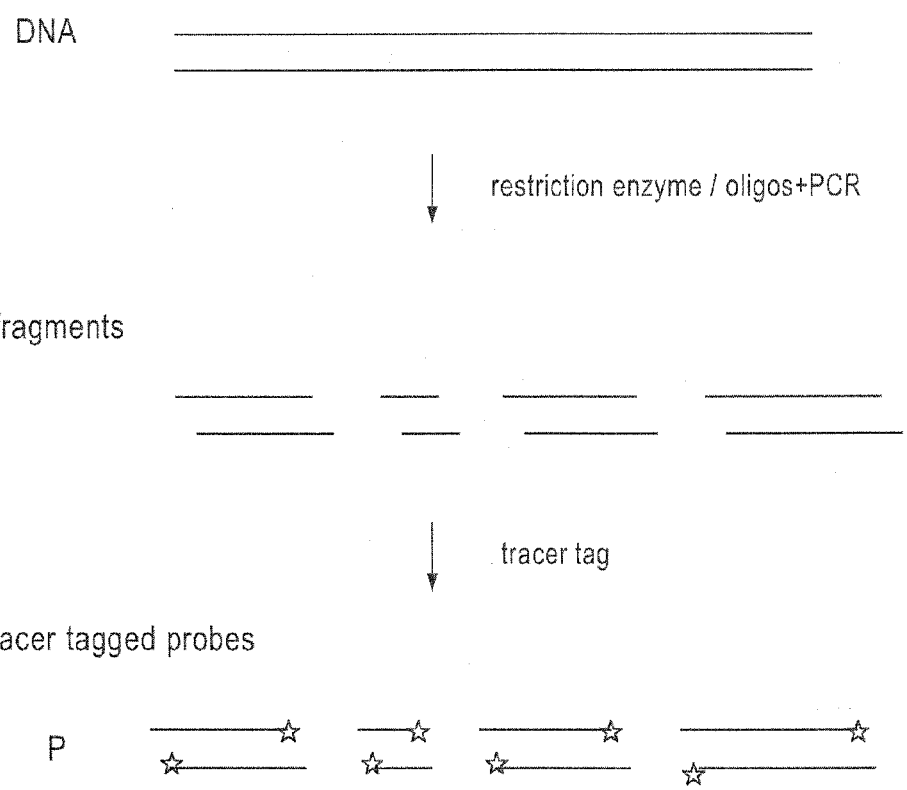
FIG. 1 is a schematic illustration of the method for preparing tracer-tagged probes (P).
Figure 2A:
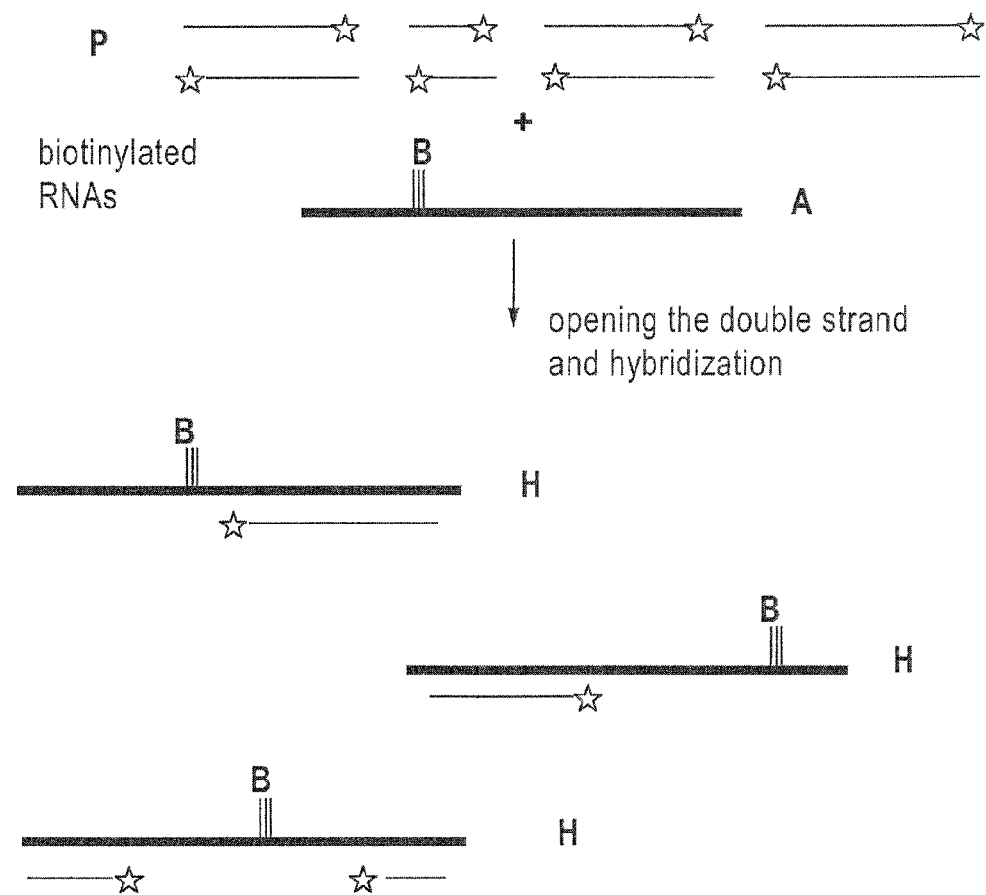
FIG. 2A illustrates the hybridization process between the tracer (star) tagged probes (P) and affinity or biotin (B) tagged single stranded RNA analyte sequences and the formation of hybrids (H) between the analytes (A) and the probes (P).
Figure 2B:
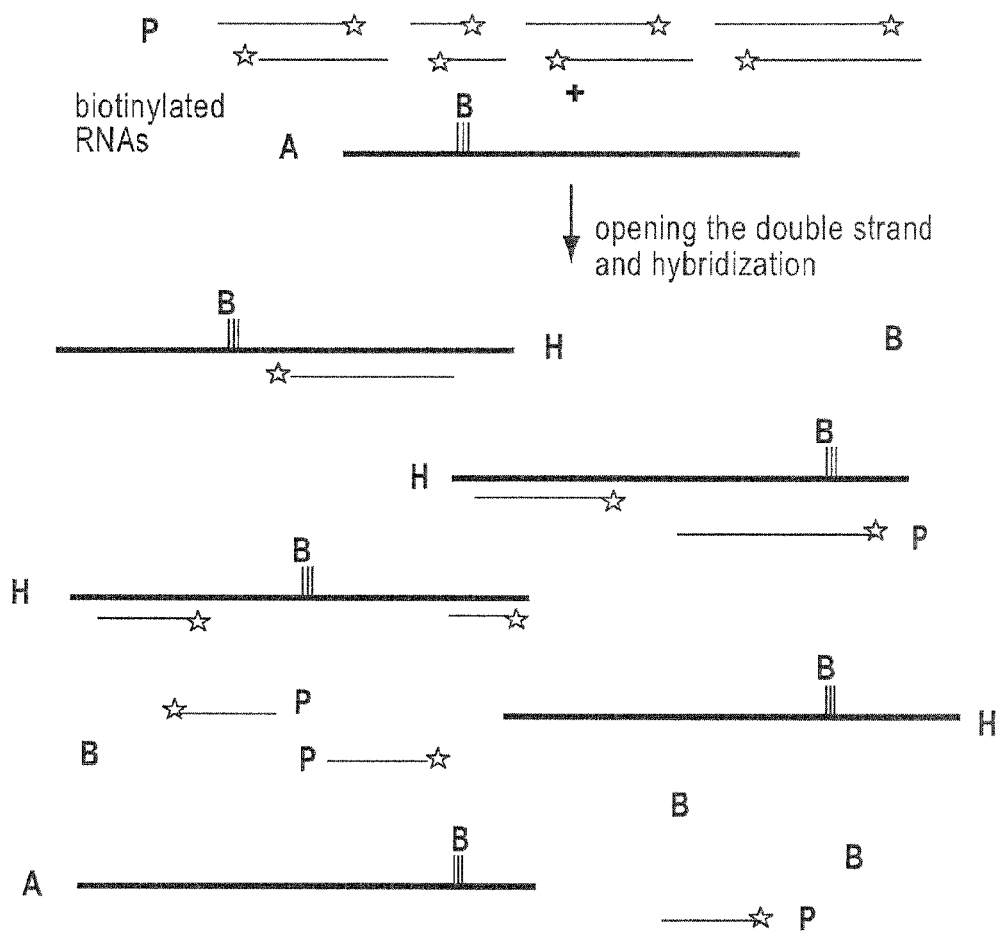
FIG. 2B illustrates the hybridization process between the tracer (star) tagged probes (P) and affinity or biotin (B) tagged double stranded polynucleotide or RNA analyte sequences and the formation of hybrids (H) between the analytes (A) and the probes (P). Probes, which do not match analyte sequences, or which are present in molar excess, remain free in solution.
Figure 3A:
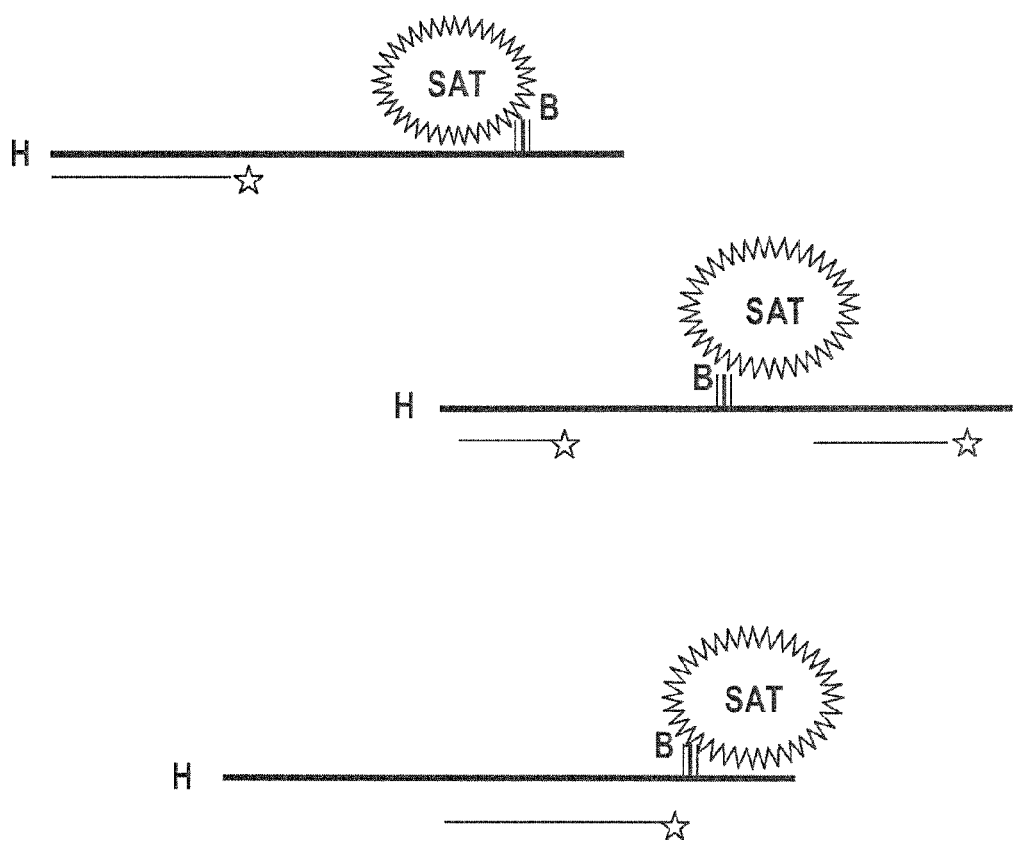
FIG. 3A depicts the capture of the affinity (B) tagged hybrids (H) to a solid separation aiding tool (SAT) covered with the counterpart of the affinity tag (B).
Figure 3B:
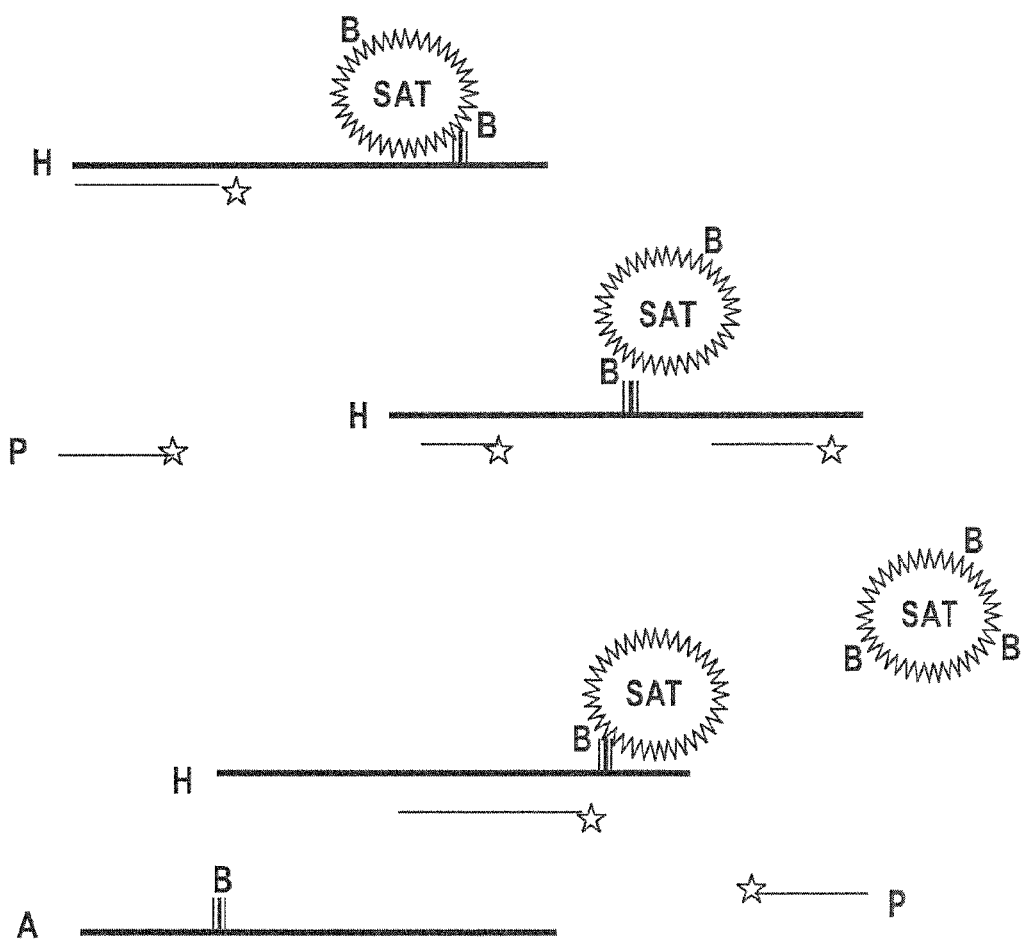

FIG. 3B depicts the capture of the affinity (B) tagged hybrids (H) to a solid separation aiding tool (SAT) covered with the counterpart of the affinity tag (B). Tracer tagged probe sequences which have not hybridized with an affinity tagged analyte sequence are not captured. Naturally, the separation aiding tools (SAT) bind free affinity tag as well as such affinity tagged analytes to which no probe sequence has hybridized.

Figure 4:
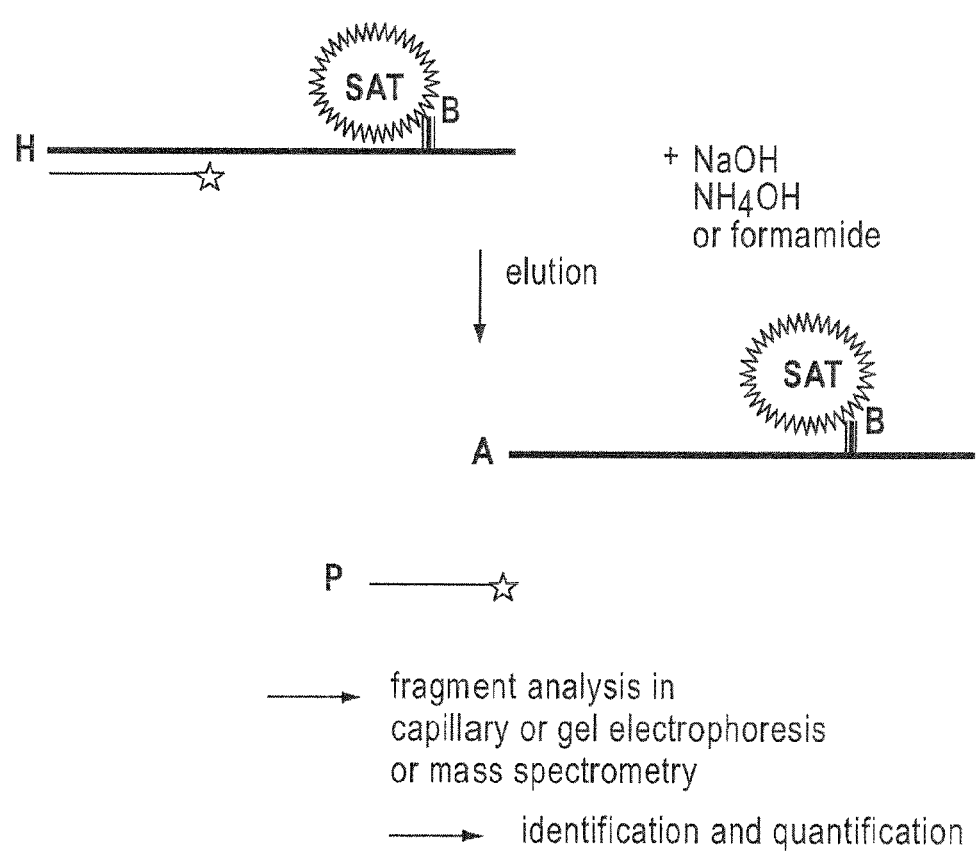

FIG. 4 depicts release using elution of the tracer tagged probes (P) from the solid separation aiding tool (SAT)/leaving the affinity tagged analyte sequence (A) with the separation aiding tool (SAT) and tracer tagged probe (P) in solution.

Figure 5:
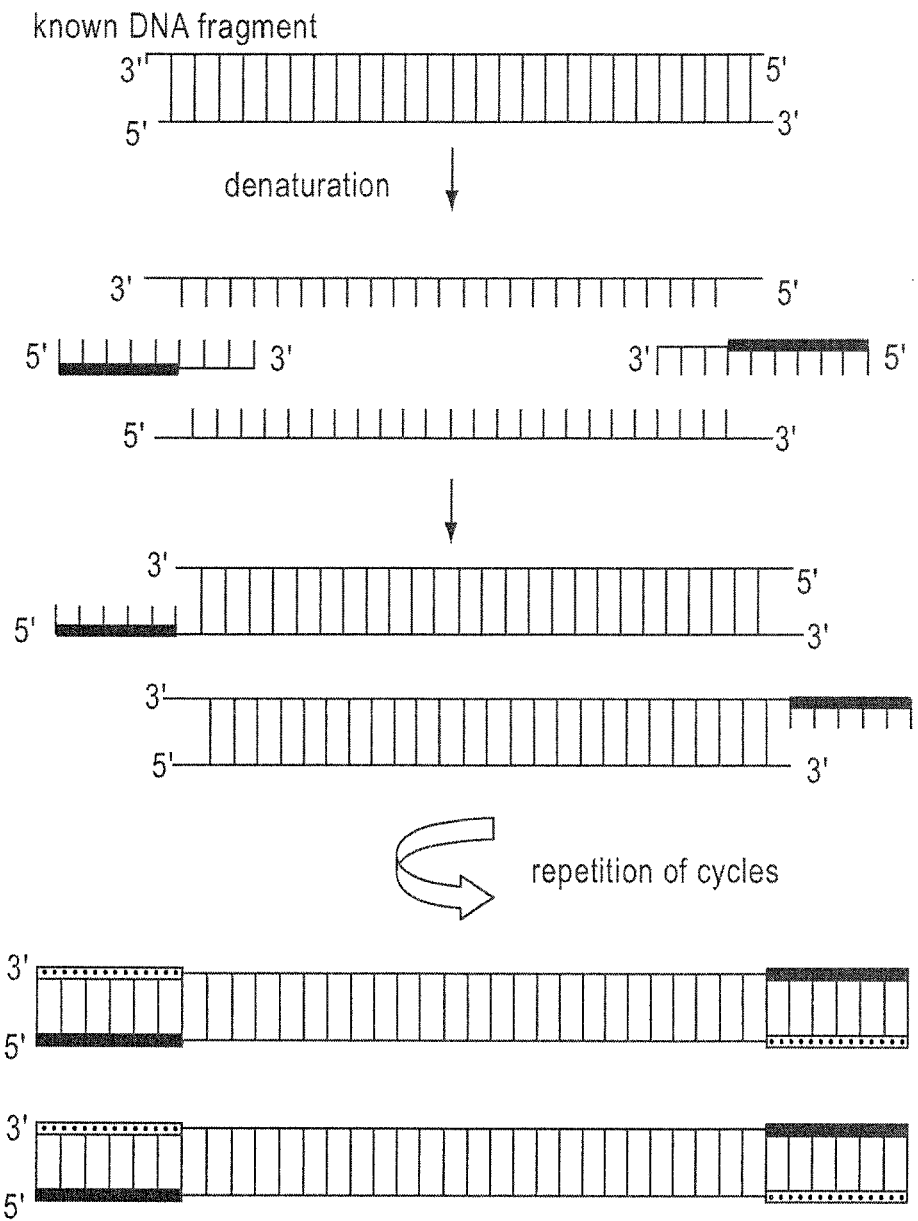

FIG. 5 depicts the PCR-synthesis of probes by primers with additional 16-mer identical sequences or terminal primer tags (TPTs).

Figure 6:
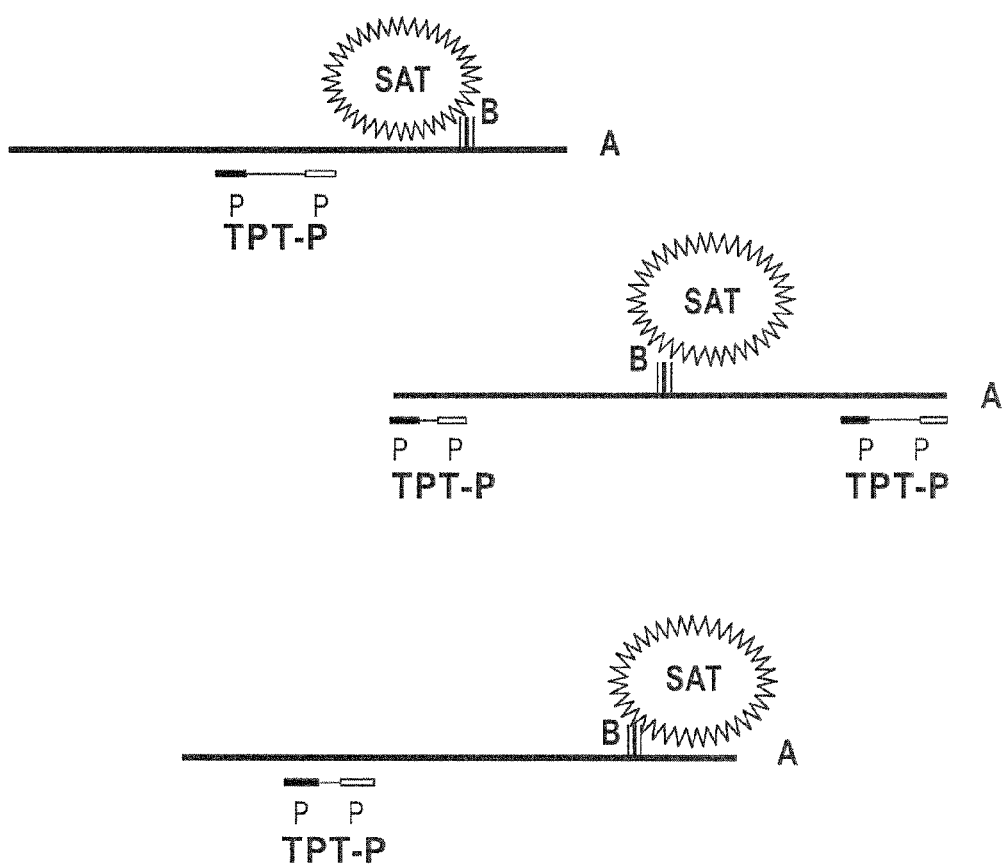

FIG. 6 depicts the capture of terminal primer tagged probes (TPT-P): affinity (B) tagged analyte (A) on a separation aiding tool (SAT). The terminal primers in each end of the terminal primer tagged probes (TPT-P) are marked with (Ps) as well.

Figure 7:
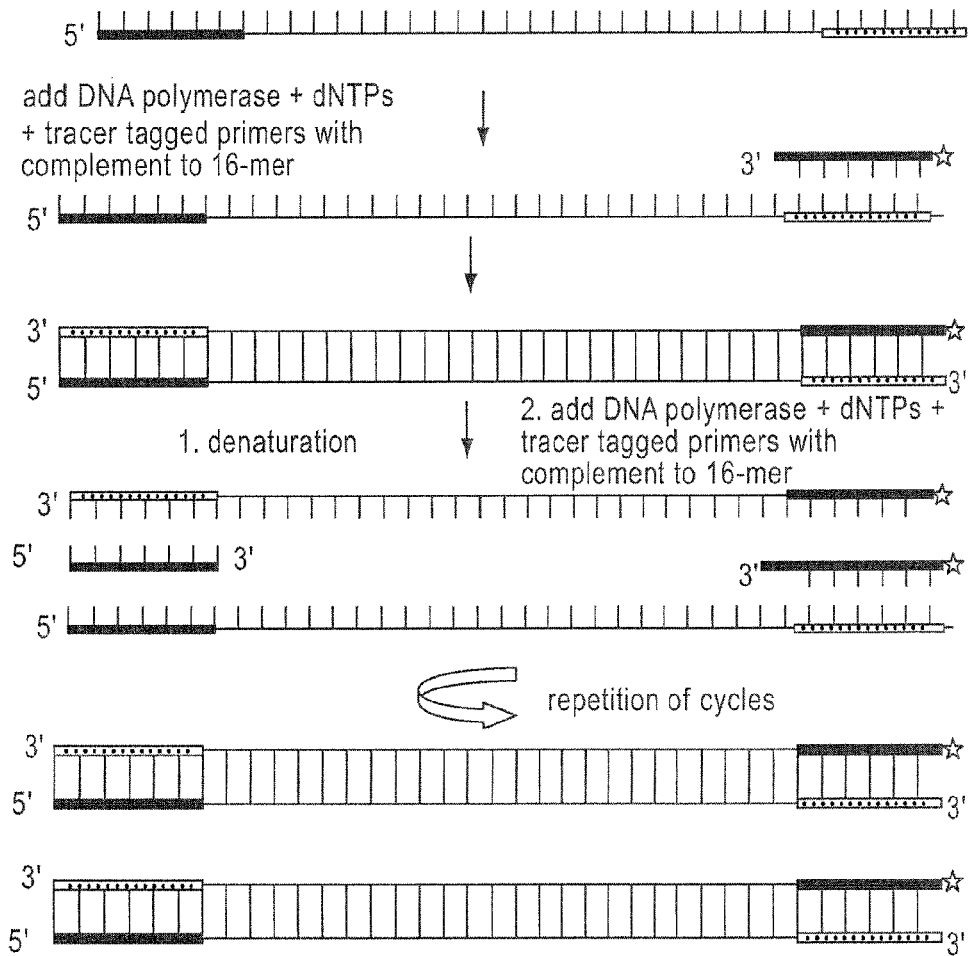

FIG. 7 illustrates the PCR-amplification of eluted terminal primer tagged probes (TPT-Ps) with tracer (star) tagged primers.

Figures 8A, 8B, 8C:
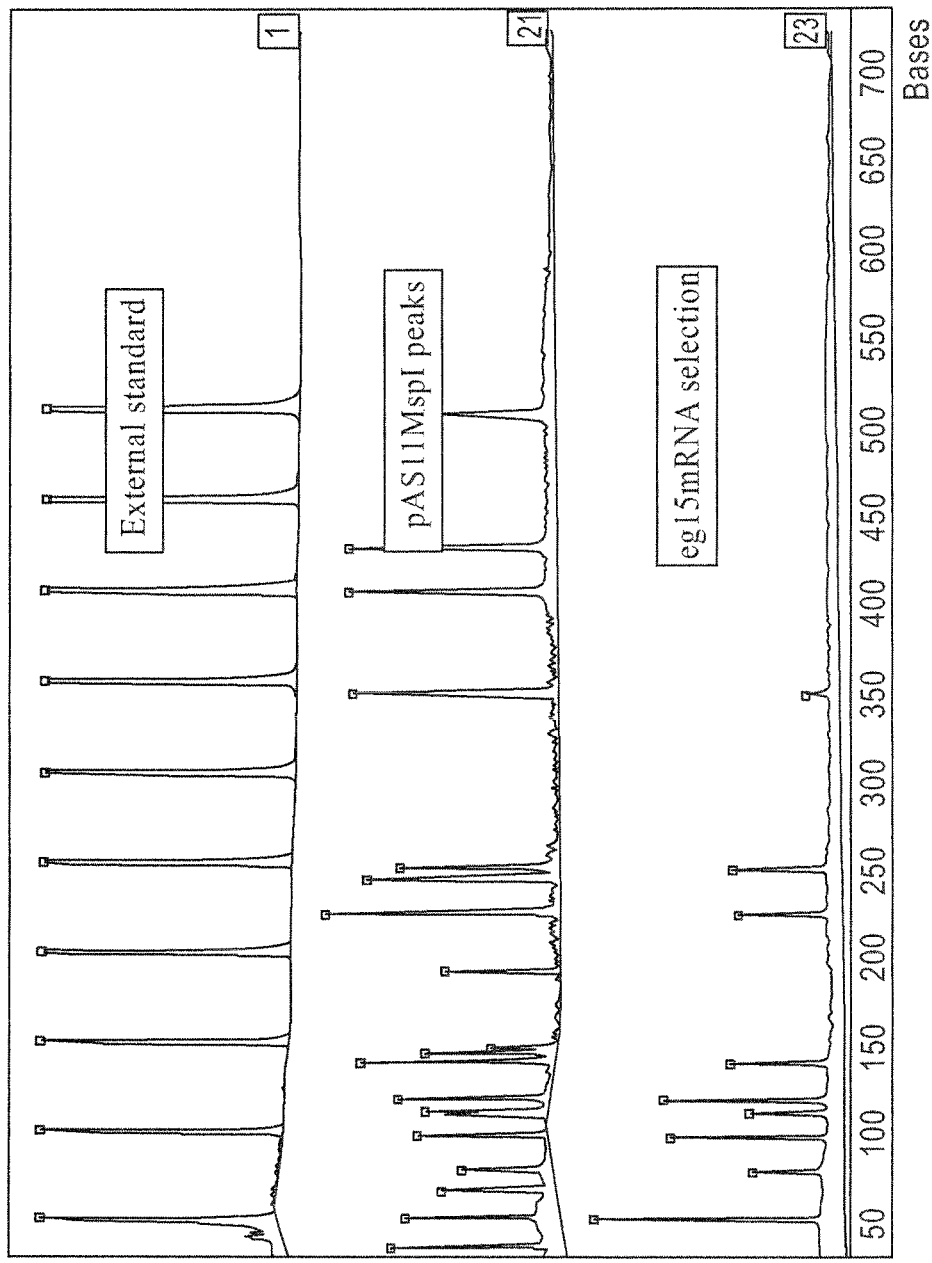

FIGS. 8A-8C shows the results, which can be recorded from an electropherogram and from a data file obtained when carrying out the quantitative process of the invention according to Example 1.

FIG. 8A shows the result recorded with an external standard.

FIG. 8B shows the results recorded of all peaks obtained from pAS11MspI.

FIG. 8C shows the results recorded from the egl5 mRNA selection.

Figure 9A:
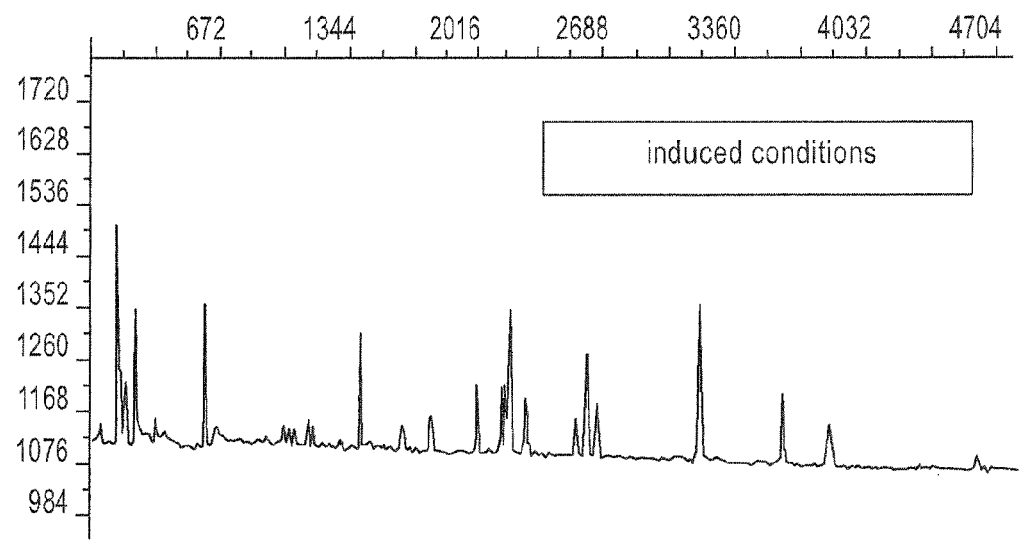
Figure 9B:
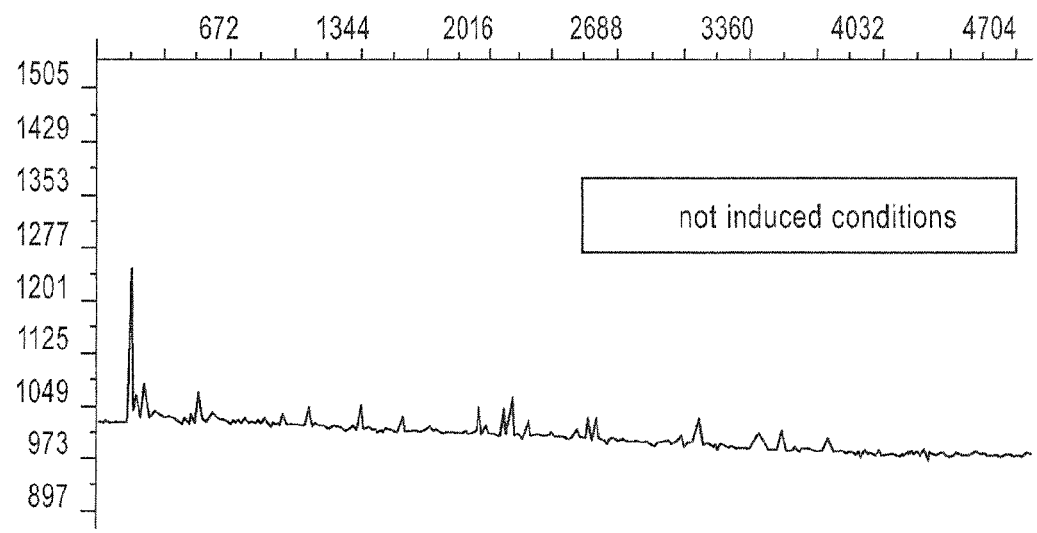

FIGS. 9A-9B shows the results, which can be recorded from an electropherogram and from a data file obtained when carrying out the comparative process of the invention according to Example 2.

FIG. 9A shows the results obtained when using induced conditions.

FIG. 9B shows the results obtained under non-induced conditions.

Figure 10:
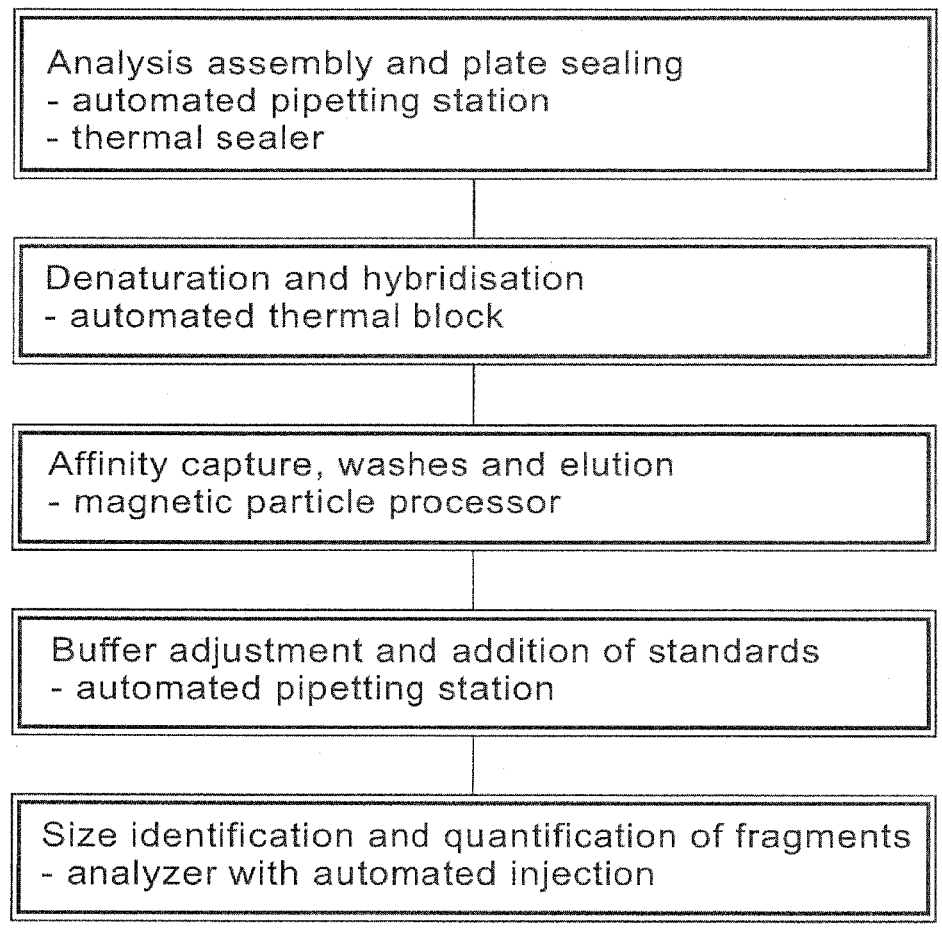

FIG. 10 shows a semi-automated performance of the process as a flow sheet.

A DETAILED DESCRIPTION OF THE INVENTION

The terms used in the present invention have the meaning they usually have in the fields of recombinant DNA technology and nucleic acid hybridization technology. Some terms in the present invention are, however, used in a broader or somewhat different manner. Therefore, some of the terms are defined in more detail below.

DEFINITIONS

The term "pool" means a subset or a library of soluble or solubilizable polynucleotide probes. Each pool comprises an optional defined number of polynucleotide probes. A convenient optional number is, for example, approximately 10 probes. However, the method can be used with as few as two or three probes, but a convenient number of probes is five or more probes in each pool. Test kits with pools comprising hundreds of soluble probes can be prepared and used in the quantitative or comparative method of the present invention. Even if it is possible to prepare pools comprising thousands of probes, a preferred upper limit seems to be approximately 300-500 different probes in order to obtain satisfactory resolution.

As said above the "soluble or solubilizable probes" are characterized by having distinct sizes, which enable their accurate identification when recording the results by optional automatic or semiautomatic means or instruments, including mass spectrometry. The sizes of the soluble probes may vary between approximately 16 bp up to several thousands of nucleotides.

The "soluble probes" for the pools may be prepared from a characterized, partially characterized or a completely uncharacterized library of polynucleotide sequences, e.g. DNA-fragments from the genome of the target organism, the transcription profile of which is to be determined. In the case of well characterized genomes, the probes are preferably arranged in pools so that all the probe molecules have a distinct or characteristic size, which enables their identification by their size or mass, e.g. using capillary or gel electrophoresis or mass spectrometry. Pools of poorly characterized genomes are in the same manner designed to contain a number of nucleic acid fragments with distinct sizes. However, because the nucleotide fragments are not characterized, some of the nucleotide fragments obtained by cleaving with various restriction enzymes may by chance have identical sizes. This means that the probes are only partly identifiable by their sizes. When repeating the tests, the redundancy is soon detected and such probes, which cannot be identified with 100% accuracy may be deleted or replaced with other more convenient probes. Even with a fully uncharacterized genome a lot of information can be accumulated in a short time and at least those parts of the genome, which are used for preparing the soluble organized pools, will soon be well characterized.

The "soluble organized pool" comprising "soluble or solubilizable polynucleotide probes" may be contained in any kind of vessels, which may be totally separate or connected either in a non-fixed or a rigidly fixed manner. In its simplest form, an organized pool comprises one or more vessels, for example test tubes or bottles, which can be connected together in a non-fixed manner for example in a rack for test tubes. A practical example of organized pools placed in vessels, which are connected together in a rigidly fixed manner is provided by the compartments or wells in or on a microtiter plate. As said above the soluble pools are preferably placed in an organized manner, e.g. in the wells on the microtiter plate. The soluble pools are organized in such a way that each pool and each polynucleotide probe in said pool is distinctly identifiable. Microtiter plates with their wells are typical, commercially available embodiments allowing organization and simultaneous handling of many organized pools. Naturally, other tailor-made more convenient organized pools with multiple compartments can be developed and constructed and provided with appropriate marks and instructions for use.

The "probes" or "pool of probes" means a set of soluble polynucleotide sequences, i.e. DNA fragments, which preferably are obtainable from genomic DNA sequences of the target organisms, which sequences may be characterized, partially characterized or uncharacterized. The probes can, for example, be cDNA copied from characterized, partially characterized or uncharacterized mRNA. The probes can conveniently receive their distinct size by cleavage With restriction enzymes, or by amplifying them using the PCR reactions with suitable primers. The probes can also be synthesized oligomers prepared with natural DNA as models.

Alternatively, DNA probes having random sequences with distinguishable sizes can be prepared and used to study specific expression patterns. Naturally, if a set of oligonucleotide probes is prepared synthetically, it is also convenient to prepare modified polynucleotide probes, in which case the sugar phosphate backbone of the nucleotide sequences can be replaced by peptide bonds or made of so called locked nucleoside analogs. Modified polynucleotides are, for example, peptide nucleic acids (PNAs) described e.g. in WO 96/20212 or locked nucleic acids (LNA), described e.g. in WO 99/14226. Said modified polynucleotide probes can conveniently be applied in the method and test kits of the present invention. They can be copied using genomic DNA or cDNA as models. Often, they have improved properties, including improved stability and they may also have the advantage of being more easy to provide with tracer tags than natural DNA probes.

The prerequisites of the present invention are that the probes in the soluble pools have distinct sizes meaning distinguishable molecular masses. The probes can optionally be provided with a "tag", which means a label or marker, which enables the detection or recording of the probe or alternatively the amplification of the probe. In the basic embodiment of the present invention the tag is a tracer, i.e. a detectable or recordable marker or label such as a fluorophor. It is to be noted that the tracer tag is preferably placed in one end of the probe, e.g. it is end-tagged, in order to prevent the tracer from disturbing the hybridization reactions between the probe and the analyte.

In a more advanced embodiment of the present invention allowing not only a quantitative assessment, but also providing a far more sensitive test, the "tag" comprises "a pair of terminal primer sequences", and optionally a tracer. These primer tags placed in the 3'- and 5'-terminal ends of the probe allow amplification of the probes after a quantitative recovery of the probes hybridizing with the affinity tagged analytes. In this embodiment the probes can be provided with an optional tracer tag during or after the amplification. If mass spectrometry is used for recording, no tracers are needed.

The term "tracer tags" means labels or markers, which are visible or otherwise detectable, i.e. recordable as such or which can be made detectable or recordable when contacted with other reagents. The tracer tags recordable by their electrochemical or magnetic, including mass spectrometric properties, fluorescence, luminescence, infrared absorption, radioactivity or by enzymatic reactions are especially appropriate, but any tracer tags, which are easily recordable by automatic means or instruments can be used. It is to be noted that no tracer tag is needed if mass spectrometry is used for recording because the probes are distinguishable by their distinct sizes.

Preferred tracer tags are fluorochromes or fluorophors, especially such which have different wave-lengths of emission. Said fluorescent label may be e.g. thiolreactive fluorescent dyes, such as 5-(2-((iodoacetyl)amino)ethyl)aminonapthylene1-sulfonic acid) (1,5-IEDANS), fluorescein, Bodipy, FTC, Texas Red, phycoerythrin, rhodamines, carboxytetramethylrhodamine, DAPI, indopyras dyes, Cascade Blue, Oregon Green, eosins, erythrosin, pyridyloxazoles, benzoxadiazoles, aminonapthalenes, pyrenes, maleimides, coumarins, MBD, Lucifer Yellow, Propidium iodide, porhyrins, CY3, CY5, CY9, lanthanides, cryptates, lanthanide chelates, or derivatives or analogues of said tracer molecules. The fluorescent polynucleotide probes are especially useful in automatic or semiautomatic recording of the results combined with continuous flow systems and instruments.

The term "analytes" means the polynucleotide sequences, especially messenger RNA (mRNA) present at a certain moment in the cell or tissue sample of the research object or subject of the study. The sample preparation comprising the analyte polynucleotide sequences is modified to include a suitable affinity tag.

The term "affinity tags" means that the analyte polynucleotides are provided with a label or marker, which has a high affinity to another substance. In other words, the affinity tag is prone to form strong bonds with its counterpart or affinity pair. The strong bonds formed between affinity pairs enables the affinity-pair to act as means for capturing desired substances. A useful affinity pair is for example biotin-avidin or biotin-streptavidin, but other synthetic or non-synthetic "affinity pairs" or binding substances can also be applied. Suitable "affinity pairs" can be found among receptors and ligands, antigens and antibodies as well as among fragments thereof. The preferred "affinity tags" of the present invention include smaller molecules such as biotin, histidine oligomers, haptens, glycans, etc., whereas the preferred counterparts of the "affinity tags" include bigger molecules such as avidin, streptavidin, metal chelates, antibodies, lectins, etc.

Preferably the analyte polynucleotides are affinity tagged by a chemical reaction, in which e.g. biotin residues are covalently linked to the polynucleotides or nucleic acid molecules to be studied resulting in a modified polynucleotide analyte, i.e. a biotinylated polynucleotide analyte. In order to avoid that steric hindrances disturb the hybridization reaction between the tracer tagged probe and the polynucleotide analyte, the polynucleotide analytes are tagged with the smaller counterpart of the affinity pair, whereas its bigger counterpart is attached to a solid support or separation aiding tool. For studies relating to transcriptional profiling the affinity-tagged analyte polynucleotide sequence is typically a mRNA preparation. The affinity tag and its counterpart or pair provides a so called affinity-pair, which allows the capture of affinity tagged substances to a solid support, which in this case is called a separation aiding tool.

The term "separation aiding tool" means preferentially solid supports, such as microbeads, latex particles, magnetic particles, threads, pegs, sticks, microwells, affinity columns, which are provided with or covered with the counterpart or affinity pair of the "affinity tag". Optionally, the separation aiding tool can include e.g. phase separation or electrophoretic means, which are dependent on the presence of the counterpart of the affinity tag.

The term "target organism" means any unicellular or multicellular organisms with characterized, partially characterized or uncharacterized genomes, the transcription profiles or expression patterns of which are to be determined. Unicellular organisms include microorganisms, such as bacteria, e.g. *Escherichia coli*, yeasts, e.g. *Saccharomyces cerevisiae* or filamentous fungi. The target organism can naturally be cells or tissue samples from any plant or animal including human beings. The genomes of *E. coli*, *S. cerevisiae* and human beings are examples of genomes which at present are more or less fully characterized.

The General Description of the Invention

The present invention is related to a method for quantitative determination of amounts of various polynucleotides present in a cell or tissue sample and variations in the amounts due to inherent causes or external stimuli. In the basic embodiment of the method of the present invention a hybridization reaction is allowed to take place in a solution and the hybrid formed is captured on a solid support provided with or covered with the counterpart or affinity pair of the affinity tag. The covering is achieved by chemical means, e.g. by conjugation. Sometimes the affinity between the surface(s) of the solid separation aiding tool and the counterpart of the affinity tag is sufficient to form a stable binding. Tracer-tagged, preferably end-tagged polynucleotide probes from a previously characterized, partially characterized or uncharacterized pool (library) are contacted with the affinity-tagged polynucleotide sequences obtained from the sample to be analyzed, i.e. the analytes.

One or more soluble pools are provided with preset, but optional numbers, preferably varying between 10-500, more preferably between 50-400, most preferably between 100-300 soluble polynucleotide sequences, with distinct sizes allowing their accurate identification, e.g. by mass spectrometry. The soluble probes, which can be identified without any tracer tags, can alternatively be provided with tags, which in the basic embodiment of the present invention are detectable or recordable tracers and in an advanced embodiment allowing a more sensitive assessment, a pair of terminal primer tags, which enable an amplification reaction during which the probes can be provided with a tracer tag using e.g. tracer tagged primers or labeled nucleotides. The soluble pools are placed in an organized manner in their own vessels, which can be separate, loosely connected or removable. The organized pools can also be place in or on a more compact structure, wherein the vessels are more or less rigidly joined together as the wells on a microtiter plate.

In the method of the present invention the pools of soluble polynucleotide sequences are obtainable from characterized, partially characterized or uncharacterized genomes. Generally, one probe corresponding to each gene in a characterized genome is sufficient for a quantitative determination of its expression. A pool is generally prepared by restriction enzyme fragmentation of a genomic insert. The insert is placed into a plasmid for convenient multiplication. The probes are constructed by fractionating selected polynucleotide sequences with restriction enzymes. Thus, one convenient way of preparing the probes is to insert the polynucleotide sequence into a plasmid, to multiply said plasmid, and thereafter, to cleave said plasmid with its insert. Alternatively, probes can be prepared from genomic DNA or cDNA libraries using PCR reactions or amplification. As the aim of the present invention is to assess simultaneously the expression of more than one gene, each pool usually comprises more than one, preferably at least ten, most preferably about hundred or more probes.

If the analyte polynucleotides are for example expression products from an uncharacterized genome, at least one probe for each gene to be quantified in the uncharacterized genome should be used. This means that organized pools from partially characterized or uncharacterized genomes should be prepared from more than one plasmid, preferably from at least two plasmids. The genomic inserts of the plasmids should preferably be different, but they can be prepared from the same insert, in which case they may have some partly overlapping sequences. If the probes are produced from plasmids comprising the same sequences, different restriction enzymes can be used in order to obtain the probes with distinct sizes required in of the present invention.

When uncharacterized genomes are the object of the study and no commercial test kits are available, it is to be recommended that a large set of identical organized pools are prepared at one time, in order to avoid the need of repeating the tedious preparative step and enable concentration on the analytical step. This is also the basis for providing commercial test kits for studying partially characterized or uncharacterized genomes.

In the basic embodiment of the present invention tracer or primer tagged DNA probes are allowed to hybridize with the preparation of RNA, which is to be analyzed. The analyte polynucleotide sequences or RNA analytes, present in the cell or tissue sample to be determined, are isolated by per se known methods. Generally the analyte polynucleotides to be determined from the cell or tissue sample, are messenger RNAs (mRNA). Said analytes are provided with at least one affinity tag, such as biotin, histidine oligomers, haptens or glycans. The analyte polynucleotide, e.g. RNA is preferably labelled with biotin.

After these reagent preparation steps, the hybridization reaction between the probes and the analytes is allowed to take place. Thereby, hybrids are formed in a molecularly accurate quantitative manner between the soluble probes and the affinity tagged analytes. Because the amount of different probes present in the pools are known and because there is an excess of each probe as compared to the analytes, it is evident that the hybridization reaction between the analytes and the probes, which results in a hybrid is stochiometrical and the amount of probe recovered corresponds exactly to the amount of analyte polynucleotides present in the sample. Naturally, the analyte sequence need not be an expressed mRNA sequence. It is possible by the present method to quantitate any single stranded sequence as well as any double stranded sequence, after a denaturation step rendering the double stranded analyte single stranded.

As described above by the hybridization in solution DNA:RNA hybrids will form. Thereafter, the hybrids, by the aid of the RNA molecules carrying the affinity tag, preferably biotin, are collected by their affinity to their affinity pair, avidin or streptavidin. The only probes or DNA being collected on the separation aiding tool must be present in a hybrid. The collected hybrids can be washed free from excess probes, including such probes which have not been able to hybridize with an affinity tagged analyte sequence. In such cases the analyte sequence has not been present in the sample either because the gene is lacking or it is not expressed. The collected probes, which can be separated or released from the RNA is optionally provided with a tag. Redundant affinity tags and affinity tagged analyte sequences, which have not been able to hybridize, because no corresponding probes have been present in the pool are naturally captured on the solid separation aiding tool, but can be separated from the hybrids during the elution and subsequent separation processes.

Generally, the solution hybridization takes place under conditions which drive the hybridization towards the formation of hybrids, including DNA:DNA, DNA:RNA, RNA:RNA, PNA:DNA, PNA:RNA. The most preferred conditions vary depending upon the reagent probes, analytes, etc. Thereafter, the hybrids carrying the affinity-tags are isolated by collecting or capturing them on the separation aiding tool using the counterpart or affinity pair of the affinity tag. The hybrids are collected or recovered, i.e. they are removed or separated from the hybridization solution and can be washed free from other reagents. The probe molecules, which have not formed hybrids with the affinity-tagged analyte will remain in the hybridization or wash solutions and accordingly they are removed. Consequently, only those probes which have been able to hybridize to an analyte polynucleotide present in the cell or tissue sample, i.e. only those probes, which have a complementary stranded analyte present in the sample are captured by the separating aiding tool and recovered and can be collected. Naturally, such affinity tagged analytes, which do not have a complementary strand among the probes are captured on the separation aiding tool, but they do not disturb the stochiometry of the hybridization process and they do not disturb the consequent analytical steps. They can, for example, be destructed or removed when the probes are isolated or released from the hybrid. This means that the automatically or semiautomatically detectable or recordable optionally tracer tagged probes, which are identifiable by their distinct sizes, are captured or recovered and subsequently released or isolated for recording.

Only those DNA probes, which have been present in a complex or hybrid comprising an affinity tagged RNA analyte strand from the sample are collected on the separation aiding tool and subsequently isolated for recording. Optional separation aiding tools are required in the method of the present invention in order to recover the hybrids formed between the tracer tagged probes and the affinity tagged analytes. The separation aiding tools, which are solid supports, such as microparticles, microbeads, latex particles, magnetic particles, threads, pegs, sticks, microwells and affinity columns are provided or covered with the counterpart(s) or affinity pair(s) of the affinity tags. The separation aiding tool may comprise means for phase separation or electrophoretic means for capturing the counterpart of the affinity tag.

The hybrids recovered on the separation aiding tool are subsequently released from the tool first by eluting, and thereafter by breaking the hydrogen bonds of the hybrids and the optionally tagged probes which have been released from the hybrids are isolated, separated by their sizes and recorded with means allowing their quantification. Because each probe isolated represents an expressed mRNA, the expression can be quantitated on a molecular basis. Alternatively, the bonds of the hybrid are first broken and thereafter the solid support and the solution containing the probes are separated from each other by an appropriate method dependent on the separation aid used. Thereafter, e.g. by centrifugation, the probes are separated based on their size and recorded by means allowing their quantification. The purified and isolated probes on the separation aiding tools are eluted with a solution, such as NAOH, $NH_4OH$ or formamide capable of breaking the bonds between the polynucleotide strands.

If the tracer tag is lacking, the probes can be directly recorded with mass spectrometry. If the tag is a tracer, e.g. a fluorescent substance the DNA probe can also be directly recorded when it has been separated from the RNA, which does not have any tracer tag. The optionally tracer tagged reagent probes are now present in an isolated and free form and their amount corresponds exactly to the amount of analyte nucleic acid previously hybridized to them.

If the tag is a pair of terminal primers, optionally with a tracer tag, the probe can be amplified after separation from the RNA and provided with a tracer tag either during or after the amplification. For example, after an optional number of amplification cycles, the DNA probe can be provided with a tracer tag and recorded. Alternatively, the complementary primers can be provided with tracer tags, thereby the probes are provided with tracer tags during the amplification. The amplification allows the recording of expression in such minimal amounts that it is under detection limit when other methods are used. In said advanced embodiment of the present invention, which allows a more sensitive assessment of the analyte polynucleotides, the tags on the probes are terminal primer sequences. The terminal primer tagged probes are allowed to hybridize with the affinity tagged analyte polynucleotides in the same way as in the basic embodiment of the present invention. After the stochiometric hybridization reaction, the hybrids are captured on a separation aiding tool and the primer tagged probes are recovered by per se known methods. The amount of recovered probes, which exactly correspond to the amount of analyte polynucleotides present in the sample can be amplified an optional number of times by per se known PCR-techniques. Thereafter or during the amplification, the probes are provided with tracers and the amount and size of the probes is recorded. Because the recovery of the primer tagged probe is quantitative and corresponds exactly to the number of analyte molecules and it is known how many times the probes were amplified, i.e. multiplied or copied, it is easy to calculate the amount of analyte in the original sample. This allows a quantitative assessment even of such analyte polynucleotides, which without the amplification would have been under detection limit and thus not recordable. Accordingly, the sensitivity of the method of the present invention can be highly increased. This is a great advantage, if a very sensitive test is needed, for example when the clinical samples comprise only a few cells from a histological tissue specimen or a tissue biopsy.

Thus, the affinity selected probe profile can be assessed by sensitive automatic quantitative recording, after separating the probes from each other based on their size, e.g. by capillary or gel electrophoresis or mass spectrometry. A probe of a given size from a given pool corresponds to a specific analyte molecule. Hence the transcriptional profile can be very accurately deducted.

A comparative quantitative assessment of variations in the amount of various polynucleotides present in cell or tissue sample as a response to inherent changes due to inherent control mechanisms or as a response to external stimuli, including drugs, pathological states requires at least two organized soluble pools, but preferable at least one organized pool for each sample to be tested. Each pool comprise identical polynucleotide probes, but the organized pools, e.g. each on its own microtiter plate, is optionally provided with a recordable tracer tag. If tracer tags are used it is advantageous to use be distinguishable tracers, e.g. fluorophors having different wavelengths of emission. In a preferred embodiment the soluble pools are provided on microtiter plates. Each microtiter plate is otherwise identical, but each has its own specific recordable tracers, which if they are fluorophors preferably emit at different distinguishable wavelengths of emission. It is possible to compare the amounts without tracer tags using mass spectrometry and allowing computer based automatic systems to calculate and compare the recorded results.

The following flow chart of the method describes how to carry out the present invention:

Preparative Steps

Step 1—Preparation of Organized Pools of Soluble DNA Probes with Distinct Sizes

Case 1—A Known Genome (Yeast or Man)

The DNA fragments are selected to represent individual genes and their sizes are chosen to allow a good resolution in the size fractionation-stage.

Case 2—Unknown Genomes (Filamentous Fungus, *Trichoderma reesei*)

A set of representative clones of about 50 kb in size are cleaved with a suitable restriction endonuclease recognizing a 4 base recognizing restriction endonuclease site, in order to generate a set of distinct fragments. In this case, a DNA fragment may span two genes and thus hybridize with two analyte RNAs. It is possible to have several fragments for one gene. Alternatively, in some cases different fragments with identical size can be used. To cover a complete genome, redundancy is required and consequently hundreds of soluble DNA pools are needed.

Step 2—End-Labelling the DNA Probes with a Tracer Tag or a Fluorophore

Preferably, two (or more) sets of the DNA with distinguishable dyes are prepared. This allows simultaneous comparative studies of variations in expression patterns or transcription profiles due to internal mechanisms, e.g. pathological stages or due to external stimuli, such as drugs. Steps 1 and 2 are preparative and the bases for the commercially valuable test kits. The DNA pools can be made in large quantities for a large number of experiments. Accordingly, there should not be any need to repeat this rather tedious phase frequently.

Analytical Steps

Step 1 Preparation of a Single Stranded Polynucleotide Analyte

The isolation of RNA from the cells is used during appropriate experimental conditions using per se known methods (Sambrook, J. et al., Molecular cloning—A laboratory Manual, Second Edition (1989). If the polynucleotide analyte is double stranded the analyte has to be denaturated in order to provide the single stranded sequences required in the method of the present invention.

Step 2 Preparation of Affinity Tagged Analytes

The isolated mRNA is affinity tagged, for example biotinylated using a chemical, non-enzymatic process. The photoactivated reagent photobiotin is convenient for this purpose and it is commercially available. As the RNA will not be transcribed to cDNA or otherwise enzymatically modified for labelling, the RNA can be prepared and kept in strong detergents such as SDS. RNAses are inhibited by SDS so it is easy to isolate intact RNA. However, fragmentation is not a problem if not too heavy. The size of the RNA fragments will not affect the capturing capacity.

Step 3—Solution Hybridization

Contact each of the soluble tracer tagged probe (DNA) pools with an aliquot of the affinity tagged analyte (RNA) preparation. Allow the hybridization to take place in the free solution in the small volume provided in respective pool compartment. This gives a fast and quantitative reaction.

Step 4—Separation Step

Add microbeads or another separation aiding tool carrying the affinity pair, e.g. avidin to capture the RNA molecules. Wash to get rid of free DNA.

Step 5—Recovering Stage

Elute with a solution which breaks the DNA:RNA hybrid such as formamide or NaOH. If necessary, precipitate and wash the single-stranded DNA. Take up the single stranded DNA in an electrophoresis buffer. It is preferable that such conditions are used that electrophoresis of the eluate can be carried out directly and the different probes recorded simultaneously.

Step 6—Recording of Results

Determine the size and amount of DNA eluted from DNA: RNA hybrids by capillary or gel electrophoresis. Mass spectrometry can possibly be used as well. Differences in two RNA preparations are easily observed by hybridizing to DNA fragments labeled with different dyes and mixing the DNAs prior to electrophoresis.

Step 7—Interpretation of the Results

If the genome is known (case 1) the transcriptional profile becomes directly determined. In case 2 it is easy to clone and sequence all fragments with an interesting behaviour.

Step 8—Optional Amplification

If a very sensitive assay is needed the reagent polynucleotide sequences, i.e. the tracer-tagged probes eluted from the separation aiding tool can be amplified by PCR after the quantitative selection step. If this approach is used the reagent polynucleotide sequences, i.e. the probes should be modified to contain a common terminal sequence allowing amplification of all the probes in the same pool with the same PCR primer pair, provided with a tracer tag.

The fact that the probes are distinctly sized, and therefore, can be recorded based on their masses using mass spectrometry enables a further improvement of the method. By omitting the use of tracer tags, the method can be simplified and the need of expensive recordable labels can be avoided. Otherwise, the method fully corresponds to the method as described above and comprises the following consecutive steps comprising, (a) providing, one or more organized pools with a preset optional number of soluble probe polynucleotide sequences with distinct sizes allowing their identification or recording, said pools being placed in an organized manner in their own vessels which are separate or joined together;

(b) isolating the analyte polynucleotide sequences present in a cell or tissue sample of the target organism and providing said analytes with at least one affinity tag;

(c) allowing a hybridization reaction to take place between the soluble probes from the step (a) and the analyte from step (b) leading to formation of soluble probe:affinity tagged analyte-hybrids;

(d) isolating the probe:analyte-hybrids formed in step (c) by capturing said hybrid on a separation aiding tool provided with the affinity pair of the affinity tag of the analyte;

(e) recovering the probe from the separation aiding tool; and (f) recording the size and amount of probe with mass spectrometry.

Test Kits

The present invention is also related to a test kit. The test kit comprises one or more soluble organized pools with a preset optional number of soluble polynucleotide sequences or probes. The probes are optionally provided with tags, either tracer tags or a pair of terminal primer tag sequences. Preferably, the tracer tags are end-labelled detectable tracer tags.

The test kit comprises soluble organized pools, each pool having more than one, preferably more than ten, most preferably about hundred or more probes. The pools are preferably placed in an organized manner in their own vessels, e.g. test tubes, bottles or in the wells or compartments of a microtiter plate. Even if the test kit for performing the present quantitative determination is preferably a microtiter plate or a corresponding tailor-made structure, the test kit can be an optional number of test tubes, bottles, etc., which can be organized in more or less fixed arrangements, including racks and/or other rigid structures. The test kits can be customized or tailor-made and provided with appropriate marks and instructions for use.

The pools of soluble polynucleotide probes for the test kits can be prepared from fragments of DNA. They can be synthetic oligonucleotides and modified DNAs. When the test kit is prepared for studying characterized genomes, the pools of the test kit preferably comprise at least one polynucleotide fragment (probe) from each gene to be studied in the genome. Also when uncharacterized genomes are to be studied, the pools can advantageously be prepared in larger quantities, commercial production is in no way excluded, for more general or more specific studies. The pools are advantageously prepared by inserting the desired parts of the genome into a plasmid, which can be multiplied conveniently and fragmented with suitable restriction enzymes to provide the desired pools of probes with distinct sizes. The inserts can optionally be provided with desired restriction enzyme sites. Also for partially or uncharacterized genomes commercial test kits can be provided in essentially similar way. It is to be noted that even an uncharacterized genome is efficiently characterized by this method.

If the reagent polynucleotide probes are from a characterized genome each probe molecule is known to correspond to a given gene, and each probe is specifically identified by its size and pool. The transcriptional profile can thus directly be interpreted as the expression levels of the individual genes. If the reagent polynucleotide probes are poorly characterized, they are for instance derived from an organism, the genome of which is not sequenced, valuable results can still be obtained. The probe pools can in this case be created by for instance cleaving large clones of 10 to 200 kb into distinct and significantly smaller fragments. These smaller fragments are optionally labelled and utilized as probes as described above. The transcriptional profile will in this case not directly identify genes, but will give both quantitative and differential data relating to a given probe molecule. With this data in hand it is easy to clone and sequence all fragments with an interesting behaviour. Thereby a lot of information can be efficiently accumulated in a short period of time.

A preferred embodiment of the test kit can be prepared on a microtiter plate. In such a practical embodiment of the invention, pools with DNA fragments from yeast can be used for preparing the test kits. If each pool comprises e.g. 100-300 probes or fragments it gives a sufficiently good resolution. If each probe in the pool represents a given yeast gene, the approximately 6300 yeast genes can be placed on a single microtiter plate and there is still place for a number of controls. The captured DNA probes are identified partly by the pool or microtiter well to which it belongs, and partly by its size.

The optional recordable tracer tag is advantageously selected from a group of tracers detectable by fluorescence, infrared absorption, electromagnetic properties, radioactivity and enzymatic activity. The preferred tracer tag recordable by its fluorescence is a fluorochrome or a fluorophor. Mass spectroscopy is another preferred mode, which allows recording and quantification without any tracer tags. Even if tracer tags are preferred embodiments they are not essential for the method of the present invention, the only prerequisite for the test kit of the present invention is that the probes in the soluble organized pools have distinct sizes. They are optionally tagged, either with tracer tags or terminal primer tags. Accordingly, a working test kit is provided by an organized pool of terminal primer tagged probes even if no tracer is provided.

The test kit of the present invention in its simplest form is an organized pool of soluble tagged probes with distinct sizes. It is to be noted that said test kit is complete as such but can be complemented with optional tracers, affinity pairs and/or separation aiding tools. However, said auxiliary reagents are no prerequisite. Said auxiliary reagents and means for performing the method of the invention are available even commercially from several other sources. Thus, the method and test kit of the present invention can be tailor-made for the specific needs of the end-user, especially they should be applicable for automatic or semiautomatic handling.

The mode of test kit manufacturing, which accordingly need not include immobilization steps, allows for easy adaptation of tailor-made tests, directing the attention to certain subsets of genes in a given organism. The test kit may comprise an optional affinity tag for labelling the polynucleotides in the cell or tissue sample and optional separation aiding tool provided or covered with a counterpart of the affinity tag for labelling the analyte. The optional affinity pairs providing the affinity tags for the analytes and the counterparts for the separation aiding tools include, but are not limited to, for example, biotin and avidin or streptavidin, histidine oligomers and metal chelates, haptens and antibodies or glycans and lectins.

The optional separation aiding tool, which can be incorporated into the test kit or can be provided separately, is selected from a group of solid supports consisting of microparticles, microbeads, latex particles, magnetic particles, threads, pegs, sticks, microwells or affinity columns. The separation aiding tool may include means for phase separation or electrophoretic means for capturing the counterpart of the affinity tag.

For the comparative assessment of variations in expression patterns or transcription profiles organized pools with identical sets of probes can be provided. In this case, each organized pool or test kit is optionally provided with optionally different or distinguishable tracer tags, which tags preferably emit at different emission lengths. If the tags are terminal primer tags the test kits are identical, but after the amplification the recovered and/or amplified probes can be provided with distinguishable tracer tags. Alternatively, the complementary primer pair can be provided with a tracer tag, allowing tracer tagging during amplification. These auxiliary reagents can optionally be incorporated in the test kit or provided from other commercial or non-commercial sources. In order to enable simple comparative assessment of variations, in polynucleotide amounts in a sample, it is convenient to prepare test kits provided with different and distinguishable tracer tag emitting at different emission lengths and which can be recorded with automatic or semiautomatic instruments.

Test kits for comparative quantitative assessment of variations in the amounts of various polynucleotides present in cell or tissue sample as a response to inherent changes or external stimuli, including drugs, pathological states conveniently comprise at least two solid supports or microtiter plates. Each solid support or microtiter plate is provided with identical pools of polynucleotide probes, optionally provided with the tracer tags. Each solid support or microtiter plate should optionally be provided with its own distinguishable tracer tag, which allows simultaneous recording of cell or tissue samples obtained at different times, for example before or after drug treatment. Differential transcriptional profiling, i.e. analysing the differences in two or more analyte polynucleotide preparations, are easily recordable by hybridizing the analyte samples to reagent polynucleotide probes end-labelled with different, distinguishable and automatically recordable tracer tags. After the hybridization step the different samples can optionally be mixed and their differences directly observed by measuring the ratio of the tracer tags to each other in each peak. The test kit can also be provided with at least one pair of primers for amplifying the tracer tagged probes obtained in the last step, for increasing the sensitivity of the test.

The method of the present invention is useful for quantitative and comparative assessment of variations in the quantity or quality of different characterized, partially characterized or uncharacterized polynucleotides in targeted cell or tissue samples due to inherent changes or as a response to external or internal stimuli. The method and test kits can be used for evaluating the effect of treatment modalities, epidemiologic situations, hygienic conditions, microbial populations.

The test kit of the present invention in its simplest and cheapest form is otherwise the same as the test kits described above and comprises one or more organized pools with a preset optional number of soluble polynucleotide sequence probes provided with distinct sizes allowing their identification and recording with mass spectrometry. The probes can be provided with terminal primer tags in order to allow amplification before the quantitative measurement with mass spectrographic or spectrometric means. Said pools of unlabeled probes are placed in an organized manner in their own vessels, which are separate or joined together.

The test kit including the reagents of the present invention are preferably applicable for carrying out automatic or semi-automated processes, an example of which is shown as a flow sheet in FIG. 10. The process can be interrupted and the reagents transferred to other solid supports if the automatic devices are not quite compatible. The first steps are advantageously carried out in an automated pipetting station, wherein the biotinylated sample RNA is pipetted into each pool containing the distinctly sized probes in their pools. Thereafter, the test kit can be dried using a lyophilisator. The drying is made to eliminate the influence of any differences in volumes. The optional lyophilization allows the work to be stopped until it is convenient to continue the work.

The work is recontinued by adding an appropriate hybridization buffer to the pools in an automated pipetting station. The plate is sealed with appropriate means, e.g. a film or a foil in order to avoid evaporation in the subsequent step. When the test kit has been provided with an appropriate heat sealer it is positioned into an automated thermal block, where the temperature can be up- or downregulated as required to enable the denaturation and hybridization of the probes. After hybridization the solution containing the probe:analyte-hybrids are placed in a magnetic particle processor in order to carry out the affinity capture, washing and elution steps by moving steptavidin/avidin coated magnetic beads from step to step e.g. on a KingFisher plate according to a programmed protocol. The eluates can optionally be transferred into a new plate if the automated stations use different types of microtiter plates. The wells can be rinsed with elution buffer for quantitative transfer and then the combined solutions are evaporated in a lyophilisator, which enables preservation of the samples and making the recording at a more convenient time. In other words, the process can easily be adapted for different time schedules and protocols for performing the determination. The probe fragments, size standard and concentration standards, are either directly or after a convenient step, automatically injected into an automatic analyser. The intensities of labels attached to the probe fragments are determined as areas. The areas of the concentration standards, with known amounts, are then used to determine the absolute amounts each probe fragment.

The experimental design and the general principles of the present invention are described in more detail using plasmids and inserts available in the laboratory of the inventors. The plasmids are used for illustrative purposes only. The invention is in no way limited to said plasmids. The principles of the invention can be checked by replacing the construct used in the examples by any other plasmids or insert, which are available in abundance. Those skilled in the art can easily apply the principles of the invention in different applications.

Example 1

Quantitative Evaluation

A Plasmid, pAS11, Composed of a Vector Part and an Insert Part (cDNA), is Used to Create a Probe Pool.

Said plasmid was created from a pSP73 cloning vector (Promega, P2221) and from a yeast vector pAS4, containing endoclucanase-5 cDNA (Saloheimo, A., et al., Mol. Microbiol. 13, 219-228, 1994), a novel, small endoglucanase gene, egl5, from *Trichoderma reesei* isolated by expression in yeast (Saloheimo et al, 1994). The egl5-cDNA was digested out from pAS4 by EcoRI-partial XhoI-digestion, the ends were blunted by filling using Klenow Fragment (1008404 Boehringer-Mannheim) and ligated to SmaI digested pSP73 vector to create pAS11. The vector contained a T7 promoter allowing in vitro transcription. The plasmid was also used for preparing RNA in the model examples. The steps in these model experiments differed somewhat from the main steps described in the generalized method of the present invention. The experiment followed the steps set forth below:

Preparative Steps:
Step 1—Preparing Probes from Double Stranded Polynucleotides pAS11 plasmid, in DH5α cells, containing an ampicillin resistance gene were grown over night at +37° C. in LB solution containing 1% glucose and 0.1 mg/l ampicillin.
Step 2—Purification and Verification of Probe Polynucleotides Subsequently the plasmids were purified and analysed according to the Plasmid Maxi Protocol of QIAGEN® (QIAGEN® Plasmid Purification Handbook, November 1998).
Step 3—Linearization of Plasmids The purified plasmid was linearized by digestion by EcoRI, isolated by agarose gel electrophoresis and then extracted and purified using QIAquick™ Gel Extraction Kit Protocol (QIAquick™ Spin Handbook, January 1999).
Step 4—Preparation of Analytes RNA, corresponding to the insert, was prepared in vitro using RiboMAX™ Large Scale RNA Production System—T7 (Promega, P1300) and the amount produced was measured by its UV adsorption.

Analytical Steps:
Step 1—Affinity Tagging Analyte Sequences

RNA was affinity tagged with PHOTOPROBE® Biotin SP-1000 according to the manufacturer's (VECTOR Laboratories) protocol.
Step 2—Fragmentation of the Probes A sample of the plasmid was cleaved with restriction enzyme MspI to give 21 fragments, of which 10 correspond to the insert and 11 to the vector.

Step 3—End Labelling the Probe with a Tracer Tag

The DNA fragments were end-labelled with Fluorescein-12-ddCTP, NEL-400 (NEN® Life Science Products, Inc.) using Klenow Fragment (1008404 Boehringer Mannheim). The success of the labelling procedure was confirmed by analysing the DNA fragments on a gel electrophoresis DNA sequencer ALF DNA Analysis System (Amersham Pharmacia Biotech) with ALFwin Fragment Analyser 1.02 Software Package (Amersham Pharmacia Biotech) and using external control Sizer 50-500 and internal control Sizer 250 (cat. no. 27-4525-01 and 27-4527-01, Amersham Pharmacia Biotech) (FIGS. 8a and 8b).

Step 4—Solution Hybridization

An aliquot of the RNA sample (0.44 pmol) was mixed with an aliquot (0.044 pmol of each fragment) of the end-labelled DNA preparation in an RNAse free microcentrifuge tube. The concentration of SDS in the mixture was kept at 0.1%. The mixture was precipitated using 3M sodium acetate ($\frac{1}{10}\times V$) and 94% ethanol (2.5×V), pelleted (20000×g), washed with 70% EtOH and dissolved in 25 µl of hybridisation solution: 0.6 M NaCl, 20 mM sodium-phosphate (pH 7.5), 1 mM EDTA, 0.1% (w/v) SDS and 0.02% (w/v) Ficoll, 0.02% (w/v) polyvinylpyrrolidone, 0.02% (w/v) bovine serum albumin (1×Denhardt's solution). The mixture was heated to 100° C. for 3 min.

Step 5—An Optional Step Related to Hybridization

The sample was incubated at 65° C. for 2 hrs and then moved to a new RNAse free microcentrifuge tube. The incubation tube was flushed once with 25 µl of hybridisation solution and the washing solution is added to the same tube.

Step 6—Capturing Step 0.5 µl of a 5% (w/v) suspension of FLUORICON™ Avidin-Polystyrene Assay Particles (IDEXX Laboratories, 31-040-1A) were added and the incubation was continued for 30 min at 22° C. Suspension of particles was in wash solution: 20 mM sodium phosphate buffer (pH 7.5), 0.15 M NaCl, 0.1% (v/v) Tween 20.

Step 7—Separation Step

The microparticles were collected by centrifugation (12000×g, 22° C.) and washed four times with 200 µl of 0.1×SSC-0.2% SDS at 50° C. (12000×g, 40° C.).

Step 8—Elution Step

The bound DNA was eluted with 200 µl of 50 mM NaOH, precipitated, pelleted and washed as described in step 5 and dissolved in water.

Step 9—Recovering Stage

The eluted DNA was analyzed on a capillary electrophoresis DNA sequencer ABI PRISM® 310, Genetic Analyser (Applied Biosystems) using GeneScan® Analysis Software (Applied Biosystems) and a Gene Scan-500 Size Standard and known amount of a customized single size standard or on a gel electrophoresis DNA sequencer ALF DNA Analysis System (Amersham Pharmacia Biotech) with ALFwin Fragment Analyser 1.02 Software Package (Amersham Pharmacia Biotech) and using external control Sizer 50-500 and known amount of internal control Sizer 250 (cat. no. 27-4525-01 and 27-4527-01, Amersham Pharmacia Biotech).

Step 10—Recording of Results

The result was read from the electropherogram and from the data file as shown in FIG. 8c.

As seen only fragments corresponding to the insert were found as compared to FIG. 8b, in which all the fragments are shown as comparison. The quantification was calculated using the peak area of internal standard, which concentration in each sample lane was known.

Example 2

A Comparative, Quantitative Evaluation

RNA from a Filamentous Fungus *Trichoderma reesei* Before and after Induction

In this experiment RNA isolated from the filamentous fungus *Trichoderma reesei* was analysed under two different conditions, before and after induction of extracellular hydrolytic enzymes. The *Trichoderma reesei* strain used in the experiment was QM 9414 (deposited in VTT's collection as VTT-D-74075) and it is cultivated, induced with α-sophorose and harvested as described in Ilmén, M., Onnela, M.-L., Klemsdal, S., Keränen, S. and Penttilä, M. 1996. Functional analysis of the cellobiohydrolase I promoter of the filamentous fungus *Trichoderma reesei*. Mol. Gen. Genet. 253, pp. 303-314.

The total fungal RNA was prepared using the TRIzol® Reagent method (Life Technologies; Gibco BRL). Further poly (A)$^+$ RNA was isolated from total RNA using Oligotex mRNA Spin-Column Protocol (QIAGEN® Oligotex™ Handbook August 1998). This RNA was biotinylated as described in example 1, analytical step 1 above. The probe DNA fragments were the same as in Example 1. The insert in the plasmid included the gene for an endoglucanase hydrolytic enzyme, known to be induced in the conditions used.

The experiment followed the analytical steps 1-10 as described in example 1.

The electropherograms (FIGS. 9a and 9b) showed that the fragments corresponding to the endoglucanase were 3 fold more abundant after induction of extracellular hydrolytic enzymes with sophorose.

Example 3

Quantitative Evaluation of Small Amounts of Analytes

The preparative steps of the probes differed from those in examples 1 and 2 as described below in the experimental design to detect very low amounts of RNA.

The probes were prepared with a PCR reaction (see FIG. 5). For each probe fragment two unique 16-24 nucleotide long oligonucleotide sequences were selected which will specifically lead to the PCR amplification of a single DNA fragment, corresponding to a given gene. The PCR primers contained, in addition, at their 5' end another 16 nucleotide long sequence. This sequence was identical in one half of the primers, i.e. for all primers directing elongation in one direction, while another sequence was identical to the other half of the primers, i.e. for those directing elongation in the other direction. The two additional 16 mers became incorporated into all probes during their preparative amplification by PCR. In this case, the probes were not fluorophore labelled.

After the preparative procedure, in which the probe molecules were created, the experiment proceeded to the analytical part.

Step 1—Preparation of Affinity Tagged Analyte

Analyte RNA was isolated and affinity tagged with photobiotin as described in analytical step 1 in Example 1.

Step 2—Hybridization in Solution

The RNA sample was mixed with a pool of amplifiable DNA probes as described in Example 1 analytical step 4 above.

Step 3—Hybridization in Solution

The RNA sample-DNA probe mixture was incubated under conditions allowing for hybridization as described in Example 1 analytical step 5.

Step 4—Capturing

Biotinylated RNA and DNA:RNA-hybrids were collected on avidin coated particles as described in Example 1 under step 6 (FIG. 6).

Step 5—Elution

The probe DNA molecules were eluted, precipitated and washed as described in Example 1 under step 7 above.

Step 6—Amplification

A primer pair, corresponding to the common terminal 16 nucleotides of the probes was added. Primer 1 was unlabelled and added to 4×pmol/µl, primer 2 was 5' labelled with the fluorophore and was added to 50 pmol/µl. The buffer conditions were adjusted to the requirements of the used DNA polymerase (e.g. DeepVent® DNA Polymerase, #M0258L, New England Biolabs® Inc.). A PCR programme consisting of 25 cycles of e.g. 94° C., 1 min; 52° C., 30 s; 72° C., 1 min was used to amplify the probes and to introduce the fluorescent label (FIG. 7).

Step 7—Separation of Excess Primer

Excess primer was removed by vacuum filtration, for example with Millipore Multiscreen96-PCR Filter Plate, Cat. No. MANU 030 10 with a vacuum manifold MAVM 096 OR) or by gel chromatography on a spin column, for example QIAquick PCR Purification Kit, 28106) or by ethanol or propanol precipitation.

Step 8—Recording

The amplified probes were analysed by electrophoresis as described in Example 1 under step 9 above.

Example 4

Analysis Using Mass Spectrometry

For mass spectrometric analysis the probes used were synthetic oligonucleotides, in this example 30 base pairs in length. They differ from each other by their molecular mass due to differences in the sequence. Four of the probes were designed to uniquely detect one mRNA of the in vitro transcribed RNA described in example 1, while 4 were used as controls and did not have corresponding sequences in this RNA preparation. The analytical steps were as follows:

Step 1

The oligonucleotide probes were combined with the biotinylated RNA preparation of example 1 in 20 µl of the buffer described in example 1.

Step 2

The mixture was incubated at 100° C. for 3 min and at 68° C. for 4 h.

Step 3

The solution was diluted to 40 µl with adjustment of the NaCl concentration to 1 M and followed by affinity capture to streptavidine coated magnetic beads (Dynal Dynabeads M280 Streptavidin). The beads were washed four times with 0.15 M Na-citrate, 0.1% SDS at 68° C. for 15 min each, followed by two washings of the beads with RNase-free water.

Step 5

The beads were eluted with 200 µl 1 M $NH_4OH$ at room temperature.

Step 6

The elute was lyophilized.

Step 7

The lyophilized solute was suspended in 100 L ultrapure water.

Step 8

The 8 oligonucleotide probes were quantified on a MALDI-TOF Mass spectrometer. When the eight oligonucleotides with molecular weights of 9320.1, 9251.0, 9249.0, and 9257.1 (these four corresponding to the RNA) and of 8893.9, 9249.0, 9264.1 and 9296.1 (these four acting as negative controls) were analysed without affinity selection as described above. All eight masses were detected (9249.0 only once). When using the selection procedure with biotinylated RNA of example 1, only the first four oligonucleotides were identified.

Example 5

Semi-Automated Performance of the Process

The same probes and mRNA reagents as in example 1 and 2 above have been used in a semi-automated process, which is shown as a flow sheet in FIG. 10.

Step 1—Analysis Assembly and Plate Sealing

An automated pipetting station is used firstly to combine the DNA probes in the pools and secondly to add the biotinylated sample RNA into each well on the plate. The assembly is then dried using a lyophilisator to eliminate the influence of the volumes. Using an automated pipetting station the assembly is then resuspended into an appropriate hybridisation buffer, comprising for example 0.06 M Na-citrate, 0.04 M Na-phosphate pH 7.0, 0.6 M NaCl, 0.5% SDS, 20% formamide, 1×Denhardt's solution, Dextrane sulphate 2%). To avoid evaporation in the subsequent step, the plate is thereafter sealed with a film. For example a heat seal with a thermal sealer or an adhesive PCR foil seal can be used.

Step 2—Denaturation and Hybridisation

The plate is positioned into an automated thermal block, e.g. a thermal cycler, where the temperature is first raised to 100° C. to denature the double strands of the probes. Then the temperature is lowered gradually to appropriate levels, for example 68° C., allowing the hybridisation of the probe DNA and sample RNA.

Step 3—Affinity Capture, Washes and Elution

After the hybridisation a magnetic particle processor, such as KingFisher (ThermoLabsystems), is used to perform affinity capture, washing and elution steps by moving streptavidin/avidin coated magnetic beads from step to step on a KingFisher plate according to a programmed protocol. On the KingFisher plate the solutions for each step are pipetted beforehand to specified places.

After the hybridization process the contents of the plate is transferred into specified places on a KingFisher plate(s). In pursuance of rinsing the wells the solution is adjusted suitable to the affinity capture by adjusting the NaCl concentration to 1 M.

Step 4—Buffer Adjustment and Addition of Standards

The eluates are transferred into a new plate (this step is optional and used only if the automated stations use different types of microtiter plates). The wells are rinsed with elution buffer for quantitative transfer and then the combined solutions are evaporated in a lyophilisator. An automated pipetting station is used to resuspend the dried probe fragments into a running solution appropriate for the subsequent analyser (e.g. water if the analyser is the ABI 3100) and to add known amounts of size standard and concentration standards.

Step 5—Size Identification and Quantification of Fragments

The probe fragments, size standard and concentration standards are automatically injected into an analyser, such as ABI3100, Applied Biosystems or BaseStation DNA Fragment Analyzer, MJ Research Inc. The software of the analyzer is used to specify the sizes of the fragments. The intensities of the fluorescent labels attached to the probe fragments are determined as areas. The areas of the concentration standards, with known amounts, are then used to determine the absolute amounts each probe fragment.

The invention claimed is:

1. A method for quantifying multiple analyte polynucleotides that have hybridized to tracer-tagged probe polynucleotides in a sample comprising multiple sample polynucleotides including multiple analyte polynucleotides to be quantified, wherein the method comprises the consecutive steps of:
   (a) providing a probe pool comprising from 2 to 500 different tracer-tagged probe polynucleotides which are complementary to the analyte polynucleotides to be quantified, wherein the tracer-tagged probe polynucleotides in said pool are stability-providing DNA fragments, synthetic or modified oligonucleotides, which are present in excess as compared to the analyte polynucleotides to be quantified, and wherein each of the tracer-tagged probe polynucleotides has a distinct size allowing its recording;
   (b) providing affinity-tagged sample polynucleotides, including the affinity-tagged analyte polynucleotides to be quantified, by affinity tagging the sample polynucleotides with at least one affinity tag, wherein the affinity tag is a label that has affinity to a counterpart of the affinity tag and the affinity tag and its counterpart form an affinity pair thereby allowing capture of the affinity-tagged sample polynucleotides, including the affinity-tagged analyte polynucleotides to be quantified;
   (c) hybridizing the tracer-tagged probe polynucleotides to the affinity-tagged polynucleotides present in said sample, wherein said sample comprises affinity-tagged analyte polynucleotides to be quantified, wherein said hybridization leads to formation of affinity-tagged hybrids comprising complementary tracer-tagged probe polynucleotides and affinity-tagged analyte polynucleotides to be quantified;
   (d) recovering the affinity-tagged sample polynucleotides including the affinity-tagged hybrids, by capturing said affinity-tagged sample polynucleotides and said affinity-tagged hybrids on a separation aiding tool, wherein said separation aiding tool comprises counterparts of the affinity tag of the affinity-tagged polynucleotides and affinity-tagged hybrids;
   (e) washing the affinity-tagged sample polynucleotides and affinity-tagged hybrids captured on the separation aiding tool;
   (f) providing released, tracer-tagged probe polynucleotides by releasing the tracer-tagged probe polynucleotides from the affinity-tagged hybrids captured on the separation aiding tool; and
   (g) determining the size and amount of each of the released, tracer-tagged probe polynucleotides by separating said released, tracer-tagged probe polynucleotides from each other by capillary or gel electrophoresis and recording intensities of tracer tags of each of the released, tracer-tagged probe polynucleotides by automatic or semiautomatic instruments, and calculating the amounts of said released, tracer-tagged probe polynucleotides using size and concentration standards, wherein the amount of each of said released, tracer-tagged probe polynucleotides corresponds to the amount of a complementary, affinity-tagged analyte polynucleotide that was hybridized thereto.

2. The method according to claim 1, wherein the tracer tags and distinct sizes of the probe polynucleotides allow recording of the size and amount of the released tracer-tagged probe polynucleotides based on properties selected from the group consisting of fluorescence, luminescence, electromagnetic properties, and radioactivity.

3. The method according to claim 2, wherein the tracer tag recordable by its fluorescence is a fluorochrome or fluorophore.

4. The method according to claim 1, wherein the analyte polynucleotide sequences in the sample comprise mRNA.

5. The method according to claim 1, wherein the affinity tag and its counterpart form an affinity pair, and wherein the affinity pair is selected from the group consisting of biotin and avidin, biotin and streptavidin, histidine oligomers and metal chelates, haptens and antibodies, receptors and ligands, and glycans and lectins.

6. The method according to claim 1, wherein the separation-aiding tool is a solid support selected from the group consisting of microparticles, microbeads, latex particles, magnetic particles, threads, pegs, sticks, microwells and affinity columns.

7. The method according claim 1, wherein the pool is placed in a well on a microtiter plate.

8. The method according to claim 1, wherein a comparative assessment of variations in the amounts of analyte polynucleotide that have hybridized to tracer-tagged probe polynucleotides from more than one sample is performed by providing a set of test kits comprising at least one test kit for each sample to be compared, wherein each of said test kits comprises identical probe pools each comprising an identical set of from 2 to 500 different tracer-tagged probe polynucleotides, which are complementary to the affinity-tagged analyte polynucleotides to be quantified and have distinct sizes, each of the probe pools being placed in its own vessel.

9. The method according to claim 8, wherein each of the test kits are provided with pools with identical probe polynucleotides, which are soluble in the sample and wherein each of the test kits are provided with tracer tags which are distinguishable from each other.

10. The method according to claim 9, wherein each of the distinguishable tracer tags in each of the test kits is a fluorescent label emitting at a different wavelength.

11. A method for simultaneously quantifying multiple analyte polynucleotides that have hybridized to tracer-tagged probe polynucleotides in a sample containing multiple sample polynucleotides and multiple analyte polynucleotides to be quantified, wherein the method comprises the consecutive steps of:
   (a) providing a probe pool containing from 2 to 500 different tracer-tagged probe polynucleotides which are soluble in the sample and are complementary to the analyte polynucleotides to be quantified, wherein the tracer-tagged probe polynucleotides in said pool are stability providing DNA fragments, synthetic or modified oligonucleotides, which present in excess as compared to the analyte polynucleotides to be quantified, and wherein each of the tracer-tagged probe polynucleotides has a distinct size allowing its recording;
   (b) providing affinity-tagged sample polynucleotides, including affinity-tagged analyte polynucleotides to be quantified, by affinity tagging the sample polynucleotides with at least one affinity tag, wherein the affinity tag is a label that has affinity to a counterpart of the affinity tag and the affinity tag and its counterpart form an affinity pair thereby allowing capture of the affinity-tagged sample polynucleotides, including the affinity-tagged analyte polynucleotides to be quantified;

(c) hybridizing the tracer-tagged probe polynucleotides to the affinity-tagged sample polynucleotides including the affinity-tagged analyte polynucleotides to be quantified, leading to formation of affinity-tagged hybrids between complementary tracer-tagged probe polynucleotides and affinity-tagged analyte polynucleotides to be quantified;

(d) recovering the affinity-tagged sample polynucleotides, including the affinity-tagged hybrids, by capturing said affinity-tagged sample polynucleotides and said affinity-tagged hybrids on a separation aiding tool provided with counterparts of the affinity tag of the affinity-tagged polynucleotides and the affinity-tagged hybrids;

(e) washing the affinity-tagged sample polynucleotides and the affinity-tagged hybrids captured on the separation aiding tool;

(f) providing released, tracer-tagged probe polynucleotides by releasing the tracer-tagged probe polynucleotides from the affinity-tagged hybrids captured on the separation aiding tool; and (g) determining the size and amount of each of the released tracer-tagged probe polynucleotides, by separating said released, tracer-tagged probe polynucleotides from each other by capillary or gel electrophoresis and recording intensities of tracer tags of each of the released, tracer-tagged probe polynucleotides by automatic or semiautomatic instruments, and calculating the amounts of probe polynucleotides using size and concentration standards, wherein the amount of each of the tracer-tagged probe polynucleotides corresponds to the amount of each complementary, affinity-tagged analyte polynucleotide that has hybridized thereto.

12. A method for quantifying multiple analyte polynucleotides that have hybridized to terminal primer-tagged probe polynucleotides in a sample comprising multiple sample polynucleotides including multiple analyte polynucleotides to be quantified, wherein the method comprises the consecutive steps of:

(a) providing a probe pool comprising from 2 to 500 different probe polynucleotides which are complementary to the analyte polynucleotides to be quantified, wherein the probe polynucleotides in said pool are stability-providing DNA fragments, synthetic or modified oligonucleotides, which are present in excess as compared to the analyte polynucleotides to be quantified, and wherein each of the probe polynucleotides is provided with two terminal primer tags allowing its amplification and tracer-tagging, and wherein each of the probe polynucleotides has a distinct size allowing its recording;

(b) providing affinity-tagged sample polynucleotides, including the affinity-tagged analyte polynucleotides to be quantified, by affinity tagging the sample polynucleotides with at least one affinity tag, wherein the affinity tag is a label that has affinity to a counterpart of the affinity tag and the affinity tag and its counterpart form an affinity pair thereby allowing capture of the affinity-tagged sample polynucleotides, including the affinity-tagged analyte polynucleotides to be quantified;

(c) hybridizing the terminal primer-tagged probe polynucleotides to the affinity-tagged polynucleotides present in said sample, wherein said sample comprises affinity-tagged analyte polynucleotides to be quantified, wherein said hybridization leads to formation of affinity-tagged hybrids comprising complementary terminal primer-tagged probe polynucleotides and affinity-tagged analyte polynucleotides to be quantified;

(d) recovering the affinity-tagged sample polynucleotides including the affinity-tagged hybrids, by capturing said affinity-tagged sample polynucleotides and said affinity-tagged hybrids on a separation aiding tool, wherein said separation aiding tool comprises counterparts of the affinity tag of the affinity-tagged polynucleotides and affinity-tagged hybrids;

(e) washing the affinity-tagged sample polynucleotides and affinity-tagged hybrids captured on the separation aiding tool;

(f) providing released terminal primer-tagged probe polynucleotides by releasing the terminal primer-tagged probe polynucleotides from the affinity-tagged hybrids captured on the separation aiding tool; and (g) providing released, amplified and tracer-tagged probe polynucleotides by amplifying the released terminal primer-tagged probe polynucleotides using a pair of primers which are complementary to the terminal primer tags in each of the probe polynucleotides, at least one of said primers in said primer pair being provided with a tracer tag;

(h) determining the size and amount of each of the released, amplified and tracer-tagged probe polynucleotides by separating said released, amplified and tracer-tagged probe polynucleotides from each other by capillary or gel electrophoresis and recording the number of amplification cycles and intensities of tracer tags of each of the released, amplified and tracer-tagged probe polynucleotides using automatic or semiautomatic instruments, and calculating the amounts of said released, amplified and tracer-tagged probe polynucleotides using size and concentration standards, wherein the amount of each of said released, amplified and tracer-tagged probe polynucleotides corresponds to the amount of a complementary, affinity-tagged analyte polynucleotide that was hybridized thereto.

13. The method of claim 12, where the size and amount of the released, amplified and tracer-tagged probe polynucleotides are recorded by instruments detecting properties selected from the group consisting of fluorescence, luminescence, electromagnetic properties and radioactivity.

14. The method according to claim 13, wherein the tracer tag recordable by its fluorescence is a fluorochrome or fluorophore.

15. The method according to claim 12, wherein the analyte polynucleotide sequences in the sample comprise mRNA.

16. The method according to claim 12, wherein the affinity tag and its counterpart form an affinity pair, and wherein the affinity pair is selected from the group consisting of biotin and avidin, biotin and streptavidin, histidine oligomers and metal chelates, haptens and antibodies, receptors and ligands, and glycans and lectins.

17. The method according to claim 12, wherein the separation-aiding tool is a solid support selected from the group consisting of microparticles, microbeads, latex particles, magnetic particles, threads, pegs, sticks, microwells and affinity columns.

18. The method according claim 12, wherein the pool is placed in a well on a microtiter plate.

19. The method according to claim 12, wherein a comparative assessment of variations in the amounts of analyte polynucleotide that have hybridized to terminal primer-tagged probe polynucleotides from more than one sample is performed by providing a set of test kits comprising at least one test kit for each sample to be compared, wherein each of said test kits comprises identical probe pools each comprising an identical set of from 2 to 500 different probe polynucleotides, which are complementary to the affinity-tagged analyte polynucleotides to be quantified, are terminal primer-tagged and have distinct sizes, each of the probe pools being placed in its own vessel.

20. The method according to claim 12, wherein each of the test kits are provided with pools with identical terminal primer-tagged probe polynucleotides, which are soluble in the sample and wherein each of the test kits are provided with a pair of primers, which are complementary to the terminal primers in each of the probe polynucleotides, and at least one of said primers in said primer pair is provided with a tracer tag, which tracer tags in different probe pools are distinguishable from each other.

21. The method according to claim 20, wherein each of the distinguishable tracer tags in each of the test kits is a fluorescent label capable of emitting at a different wavelength.

* * * * *